US 6,713,296 B1

(12) United States Patent
Kemble

(10) Patent No.: US 6,713,296 B1
(45) Date of Patent: Mar. 30, 2004

(54) VZV GENE, MUTANT VZV AND IMMUNOGENIC COMPOSITIONS

(75) Inventor: George William Kemble, Sunnyvale, CA (US)

(73) Assignee: MedImmune Vaccines, Inc., Mountain View, CA (US)

(*) Notice: Subject to any disclaimer, the term of this patent is extended or adjusted under 35 U.S.C. 154(b) by 0 days.

(21) Appl. No.: 09/613,298

(22) Filed: Jul. 10, 2000

Related U.S. Application Data

(62) Division of application No. 08/857,534, filed on May 16, 1997, now Pat. No. 6,087,170, which is a continuation of application No. 08/235,406, filed on Apr. 28, 1994, now abandoned.

(51) Int. Cl.[7] .......................... C12N 7/04; C07K 17/00; H61K 39/12; H61K 39/25
(52) U.S. Cl. ................. 435/236; 424/204.1; 424/230.1; 530/350
(58) Field of Search ................................ 435/368, 236, 435/320.1; 424/204.1, 229.1, 430.1; 530/350

(56) References Cited

U.S. PATENT DOCUMENTS

| 4,686,101 A | 8/1987 | Ellis ............................ 424/88 |
| 4,769,239 A | 9/1988 | Ellis ............................ 424/89 |
| 4,812,559 A | 3/1989 | Ellis ............................ 536/27 |
| 4,952,674 A | 8/1990 | Keller ......................... 530/326 |
| 5,310,668 A | 5/1994 | Ellis ........................ 435/172.3 |

FOREIGN PATENT DOCUMENTS

| WO | WO 93/24616 | 12/1963 | ............ C12N/7/00 |

OTHER PUBLICATIONS

Kemble et al. Journal of Virology. 2000; 74 (23): 11311–11321.*
Takahashi, *Live Vaccine Used to Prevent the Spread of Varicella in Children in Hospital*, 1974, *The Lancet*.
Davison & Scott, Molecular Cloning of the Varicella–Zoster Virus Genome and Derivation of Six Restriction Endonuclease Maps, 1983, *J Gen Virol 64:* 181–14.
Chou, Mapping of Herpes Simplex Virus–1 Neurovirulence t $\gamma_1 34.5$, a Gene Nonessential for Growth in Culture, 1990, *Science 250:* 1262–66.
Chou & Roizman, The Terminal a Sequence of the Herpes Simplex Virus Genome Contains the Promoter of a Gene Located in the Repeat Sequences of the L Component, 1986, *J Virol 57:* 629–37.
Chou & Roizman, The $\gamma^1 34.5$ Gene of Herpes Simplex Virus Precludes Neuroblastoma Cells from Triggering Total Shut-off of Protein Synthesis Characteristic of Programmed Cell Death in Neuronal Cells, 1993, *Proc Natl Acad Sci USA 89:* 3266–70.
Cohen & Seidel, Generation of Varicella–Zoster Virus (VZV) and Viral Mutants from Cosmid DNAs: VZV Thymidylate Synthetase is not Essential for Replication In Vitro, 1993, *Proc Natl Acad Sci USA 90:* 7376–80.
Davison, Varicella–Zoster Virus, 1991, *J Gen Virol 72:* 475–86.
Davison & Scott, The Complete DNA Sequence of Varicella–Zoster Virus, 1986, *J Gen Virol 67:* 1759–1816.
Fraefel, Immediate–Early Transcription over Covalently Joined Genome Ends of Bovine Herpesvirus 1: the circ Gene, 1993, *J Virol 67:* 1328–33.
Levin, Immune Response of Elderly Individuals to a Live Attenuated Varicella Vaccine, 1992, *J Inf Disease 166:* 253–59.
Myers, Varicella in Hairless Guinea Pigs, 1991, *J Inf Disease 163:* 746–751.
Myers, Varicella in a Gorilla, 1987, *J Med Virol 23:* 317–322.
Cohen, XVIII International Herpes Workshop Abstract, 1993.
Heineman, XVIII International Herpes Workshop Abstract, 1993.

* cited by examiner

*Primary Examiner*—James Housel
*Assistant Examiner*—Shanon Foley
(74) *Attorney, Agent, or Firm*—Gwynedd Warren; Quine Intellectual Property Law Group, P.C.

(57) ABSTRACT

The invention provides for a novel VZV gene, mutant VZV and immunogenic compositions based on such novel genes and mutant VZV. Also provided are proteins, diagnostic assays and methods of producing reconstructed VZV.

8 Claims, 17 Drawing Sheets

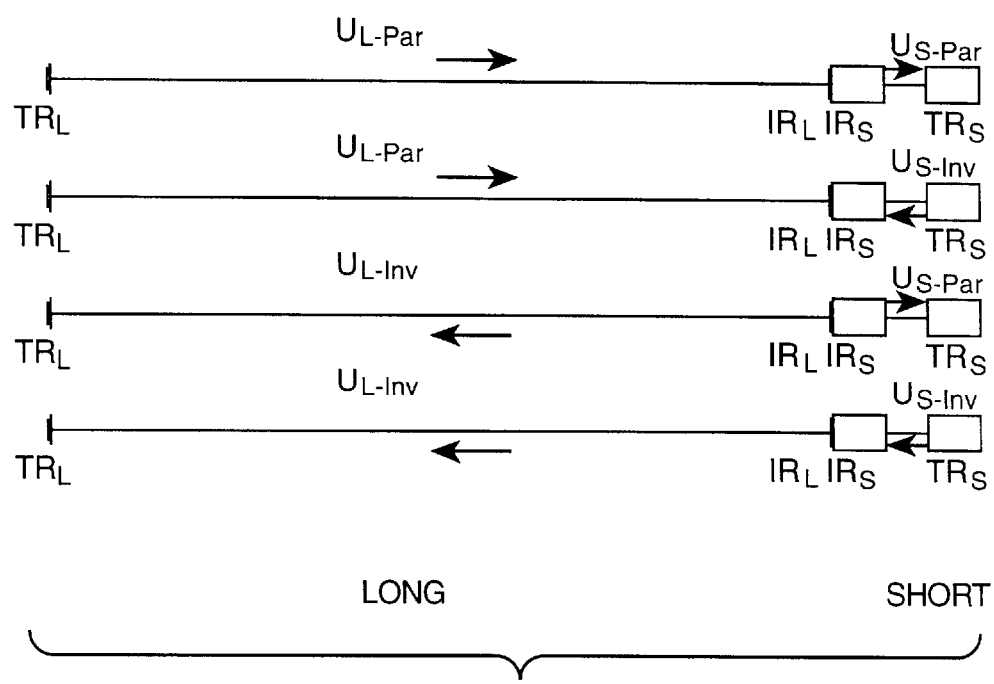
FIG._1

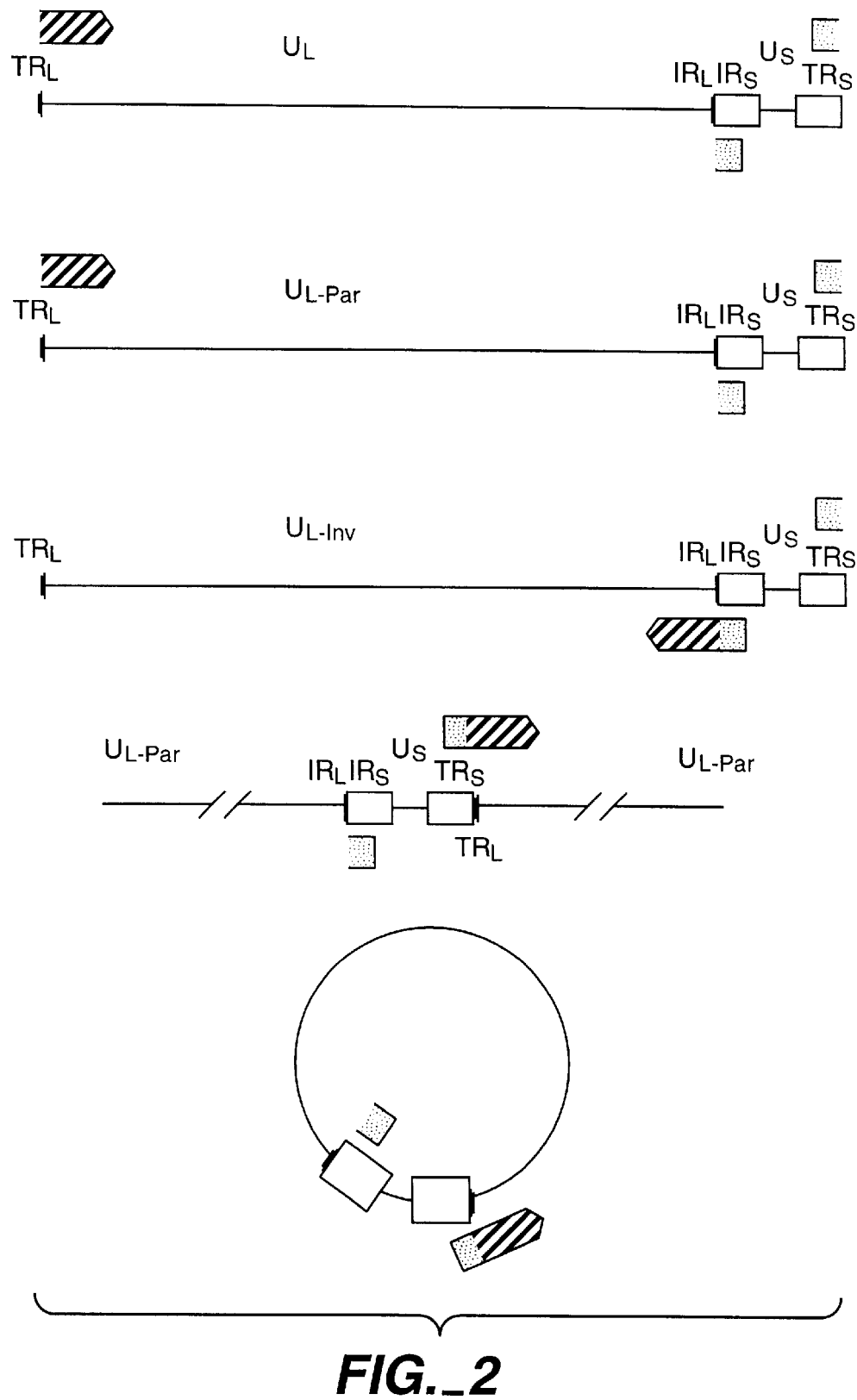
FIG._2

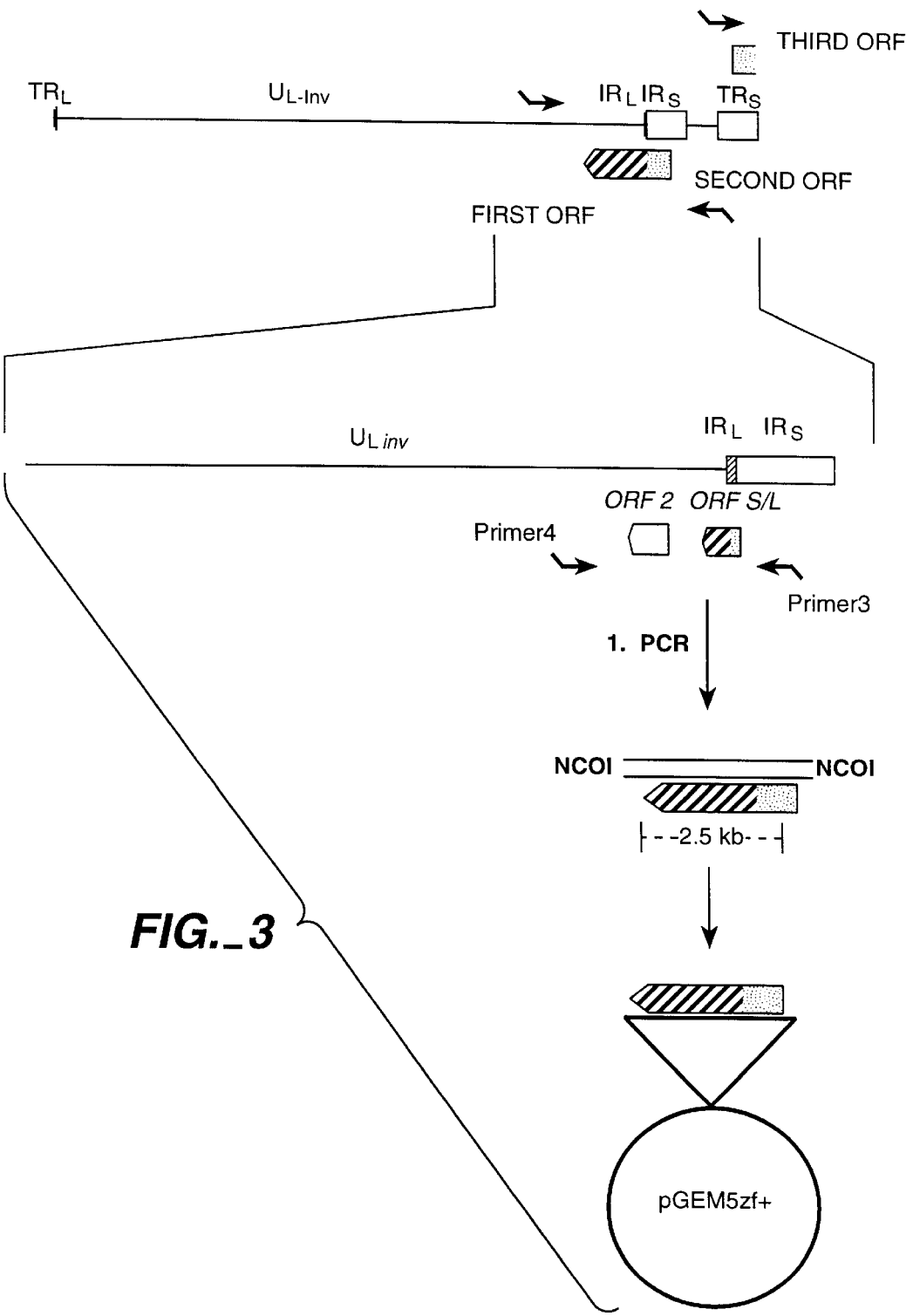
FIG._3

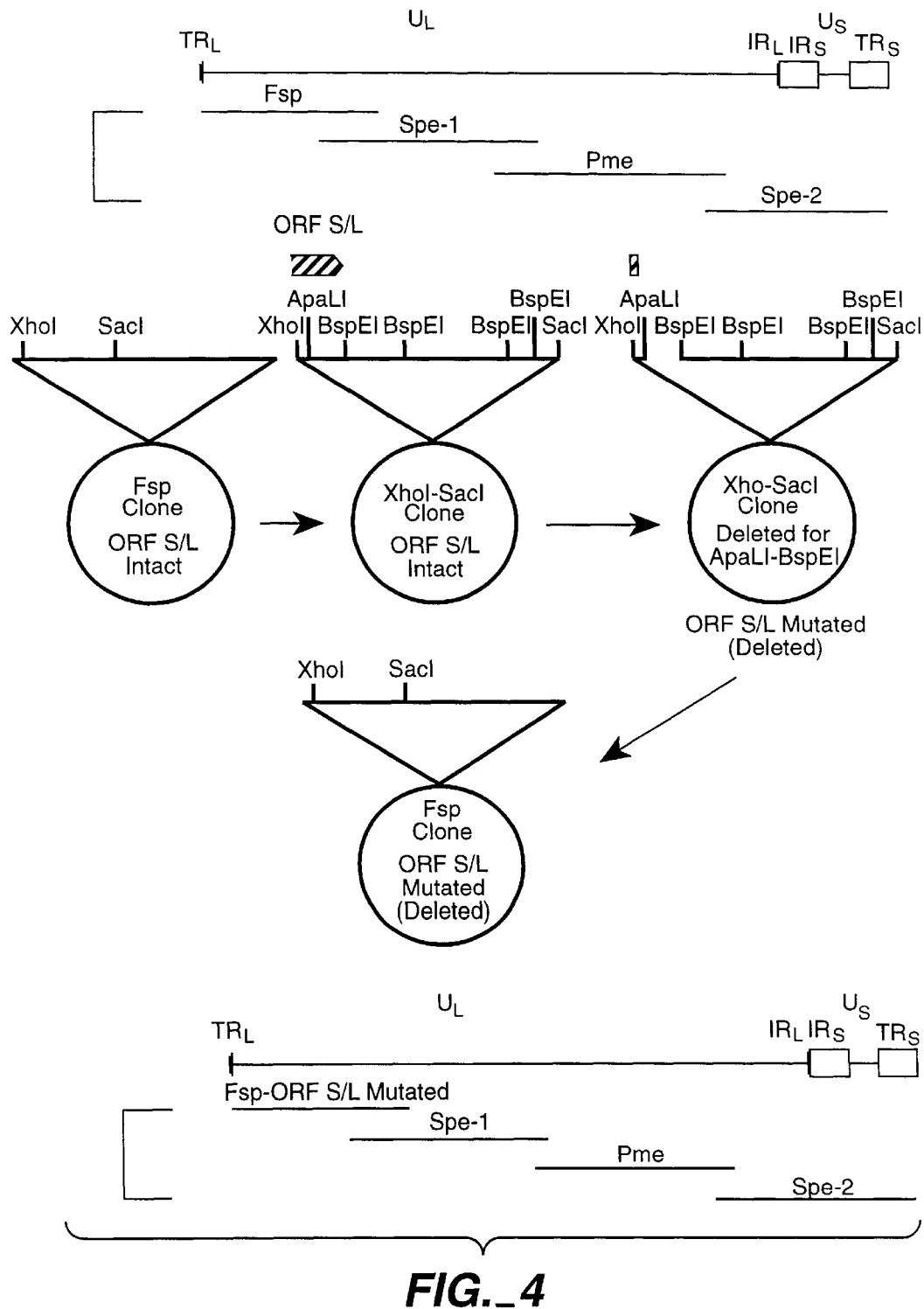
FIG._4

```
AGAGTCGGGG GTGACGGAGT CCCCTCCTTT TCTCGTGAGC GCCACTGGGCG CGCGGACTGT                    60

TTGTTGTTAA TAAAAGCGGA ACGGTTTTT ATG AAA GTG TCT GTC TGT CTG TGC                      116
                                  Met Lys Val Ser Val Cys Leu Cys
                                   1                           5

GGG CGG GCG ACG GGC GGG CTG GTC GGA CCC CCC GAA AAT AAC CCC                          164
Gly Arg Ala Thr Gly Gly Leu Val Gly Pro Pro Glu Asn Asn Pro
        10                          15                     20                25

CCC CCG GTT TCT GGG CGC CCG GCG CCG GAC CCC GGG AGA GGA GGC CAG CCC                  212
Pro Pro Val Ser Gly Arg Pro Ala Asp Pro Gly Arg Gly Gly Gln Pro
            30                          35                                  40

TCT CGC GGC CCC CTC GAG AGA GAA AAA AAG CGA CCC CAC CTC CCC                          260
Ser Arg Gly Pro Leu Glu Arg Glu Lys Lys Arg Pro His Leu Pro
        45                          50                          55

GCG CGT TTG CGG GGC GAC CAT CGG GGG GGA TGG GAT TTT TTG CCG GGA                      308
Ala Arg Leu Arg Gly Asp His Arg Gly Gly Trp Trp Asp Phe Leu Pro Gly
        60                          65                          70

AAC CCC CCC CCG CCA GCC TTT AAC AAA ACC CGC GCC TTT TGC GTC CAC                      356
Asn Pro Pro Pro Pro Ala Phe Asn Lys Thr Arg Ala Phe Cys Val His
        75                          80                          85

CCC TCG TTT ACT GCT CGG ATG GCG ACC CTC ACG TCG TCC CGC CGA CCT                      404
Pro Ser Phe Thr Ala Arg Met Ala Thr Leu Thr Ser Ser Arg Arg Pro
        90                          95                          100         105

GGG ACC CCG CCG GTC CCG ACC CTC ACG TAC TCC CCC AGC ATG GAT GAC GTT                  452
Gly Thr Pro Pro Val Pro Thr Leu Thr His Tyr Ser Pro Ser Met Asp Asp Val
        110                         115                         120

GCG ACC CCC ATC TAC CTA CCC ACA TAC GCC GAG GCC GTG GCA GAC                          500
Ala Thr Pro Ile Pro Tyr Leu Pro Thr Tyr Ala Glu Ala Val Ala Asp
        125                         130                         135
```

FIG.—5A

```
GCG CCC CCC CCT TAC AGA AGC CGC GAG AGT CTG GTG TTC TCC CCG CCT       548
Ala Pro Pro Pro Tyr Arg Ser Arg Glu Ser Leu Val Phe Ser Pro Pro
            140                 145                 150

CTT TTT CCT CAC GTG GAG AAT GGC ACC CAA CAG ACC TCT TAC GAT TGC       602
Leu Phe Pro His Val Glu Asn Gly Thr Gln Gln Thr Ser Tyr Asp Cys
155                 160                 165

CTA GAC TGC GCT TAT GAT GGA ATC CAC AGA CTT CAG CTG GCT TTT CTA       644
Leu Asp Cys Ala Tyr Asp Gly Ile His Arg Leu Gln Leu Ala Phe Leu
170                 175                 180                 185

AGA ATT CGC AAA TGC TGT GTA CCG GCT TTT TTA ATT CTT TTT GGT ATT       692
Arg Ile Arg Lys Cys Cys Val Pro Ala Phe Leu Ile Leu Phe Gly Ile
            190                 195                 200

CTC ACC CTT ACT GCT GTC GTG GCC ATT GTT GCC GTT TTT CCC GAG           740
Leu Thr Leu Thr Ala Val Val Ala Ile Val Ala Val Phe Pro Glu
205                 210                 215

GAA CCT CCC AAC TCA ACT ACA TGAAAACTACT GTCCGGAAGG GGAAGGTATT         791
Glu Pro Pro Asn Ser Thr Thr
            220

TATTCTCGCT TGCAGCTTGT CGCGCGTGTA TGCACAACAA AAGCTATATAAT ATGTCACCAA   851

AGCCAACGTC GCCATCTGGA GTACTACACC CAGTACGTTG CATAACCTGT CCATTTGCAT     911

TTTCAGTTGC GCGGACGCCT TTCTCCGGGA TCGTGGCCTT GGGACATCAA CCAGTGGAAT     971

AAGAACCGCC GGTGGTCTTG TTTGAACGAC GAGTGGCGAC GCGTTGTTCT GCATAAGCTC    1031

TGTATGCTGA TACATAAACA CAGAGTCTGT ATCGCTATCA GATTCCCGAA CACCTTCCGG    1091

TACCCCATAC TCCGATACCC TGGACATTGC GGATC                              1126
```

FIG._5B

```
AGTCGGGGGT GACGGAGTCC CCTCCTTTTC TCGTGASCCA CTGGCGCGCG GACTGTTTGT                60

TGTTTGTTAA TAAAAGCGGA ACGGTTTTT ATG AAA GTG TCT GTC TGT CTG TGC               116
                                 Met Lys Val Ser Val Cys Leu Cys
                                  1               5

GGG CGG GCG ACG GGC GGG CTG GTC GGA CCC CCG CCG AAA ATA ACC CCC               164
Gly Arg Ala Thr Gly Gly Leu Val Gly Pro Pro Pro Lys Ile Thr Pro
 10              15                  20                  25

CCC GGT TTC TGG GCG GGC GGA CCC GGA CGG GGG GGC CCA GCC CTC                   212
Pro Gly Phe Trp Ala Gly Gly Pro Gly Arg Gly Gly Gly Pro Ala Leu
         30                  35                  40

TCG CGG CCC CCT CGA GAG AGA AAA AAA GCG ACC CCA CCT CCC CGC                   260
Ser Arg Pro Pro Arg Glu Arg Lys Lys Ala Thr Pro Pro Pro Arg
 45                  50                  55

GCG TTT GCG GGG CGA CCA TCG GGG GGG ATG GGA TTT TTT GCC GGG AAA               308
Ala Phe Ala Gly Arg Pro Ser Gly Gly Met Gly Phe Phe Ala Gly Lys
         60                  65                  70

CCC CCG CCA GCC TTT AAC ACC CGC GCC TTT GTC TGC GTC CAC CCC                   356
Pro Pro Pro Ala Phe Asn Thr Arg Ala Phe Cys Val His Pro
 75                  80                  85

TCG TTT ACT GCT CGG ATG GCC ACC GTG CAC TAC TCC CGC CGA CCT GGG               404
Ser Phe Thr Ala Arg Met Ala Thr Val His Tyr Ser Arg Arg Pro Gly
         90                  95                 100                 105

ACC CCG GTC ACC CTC ACG TCG TCC CCC GGC ATG GAT GAC GTT GCG                   452
Thr Pro Val Thr Leu Thr Ser Ser Pro Gly Met Asp Asp Val Ala
                115                 120

ACC CCC ATT CCC TAC CTA CCC ACA TAC TAC GCC GAG GCC GTG GCA GAC GCG           500
Thr Pro Ile Pro Tyr Leu Pro Thr Tyr Tyr Ala Glu Ala Val Ala Asp Ala
                125                 130                 135
```

FIG._6A-1

```
CCC CCC CCT TAC AGA AGC CGC GAG AGT CTG GTG TTC TCC CCG CCT CTT        548
Pro Pro Pro Tyr Arg Ser Arg Glu Ser Leu Val Phe Ser Pro Pro Leu
                    140                     145                     150

TTT CCT CAC GTG GAG AAT GGC ACC CAA CAG TCT TAC GAT TGC CTA            596
Phe Pro His Val Glu Asn Gly Thr Gln Gln Ser Tyr Asp Cys Leu
        155                     160                     165

GAC TGC GCT TAT GAT GGA ATC CAC AGA CTT CAG CTG GCT TTT CTA AGA        644
Asp Cys Ala Tyr Asp Gly Ile His Arg Leu Gln Leu Ala Phe Leu Arg
170                     175                     180                     185

ATT CGC AAA TGC TGT GTA CCG GCT TTT TTA ATT CTT TTT GGT ATT CTC        692
Ile Arg Lys Cys Cys Val Pro Ala Phe Leu Ile Leu Phe Gly Ile Leu
            190                     195                     200

ACC CTT ACT GCT GTC GTG GTC GCC ATT GTT GCC GTT TTT CCC GAG GAA        740
Thr Leu Thr Ala Val Val Val Ala Ile Val Ala Val Phe Pro Glu Glu
                205                     210                     215

CCT CCC AAC TCA ACT ACA TGA AACTACTGTC CGGAAGGGA AGGTATTAT             790
Pro Pro Asn Ser Thr Thr Stop
            220

TCTGCTTGCA GCTTGTCGCG CGTGTATGCA CAACAAAAGC TATATATGTC ACCAAAGCCA      850

ACGTCGCCAT CTGGAGTACT ACACCCAGTA CATTGCATAA CCTGTCCATT TGCATTTTCA      910

GTTGCGCGGA CGCCTTTCTC CGGGATCGTG GCCTTGGGAC ATCAACCAGT GGAATAAGAA      970

CCGCCGGTGG TCTTGCCCGA ACGACGAGTG GCGACGCGTT GTTCTGCATA AGCTCTGTAT     1030

GCTGATACAT AAACACAGAG TCTGTATCGC TATCAGATTC CCGAACACCT TCCGGTACCC     1090

CATACTCCGA TACCCTGGAC ATTGCGGATC C                                   1121
```

FIG._6A-2

```
GGCCCAGCCCC TCTCGCGGCC CCCTCGAGAG AGAAAAAAAA AAGGGACCCCC ACCTCCCCGC                                                    60

GCGTTTGCGG GGCGACCATC GGGGGGGG ATG GGA TTT TTT GCC GGG AAA                                                            108
                                 Met Gly Phe Phe Ala Gly Lys
                                                       5

CCC CCC CCG CCA GCC TTT AAC AAA ACC CGC GCC TTT TGC GTC CAC CCC                                                       156
Pro Pro Pro Pro Ala Phe Asn Lys Thr Arg Ala Phe Cys Val His Pro
             10                          15                  20

TCG TTT ACT GCT CGG ATG GCC ACC GTG CAC TAC TCC CGC CGA CCT GGG                                                       204
Ser Phe Thr Ala Arg Met Ala Thr Val His Tyr Ser Arg Arg Pro Gly
         25                          30                  35

ACC CCG GTC ACC CTC ACG TCG TCC CCC GGC ATG GAT GAC GTT GCG                                                           252
Thr Pro Val Thr Leu Thr Ser Pro Gly Met Asp Asp Val Ala
 40                  45                  50          55

ACC CCC ATT CCC TAC CTA CCC ACA TAC GCC GAG GTG GCA GAC GCG                                                           300
Thr Pro Ile Pro Tyr Leu Pro Thr Tyr Ala Glu Val Ala Asp Ala
         60                  65                  70

CCC CCC CCT TAC AGA AGC CGC GAG AGT CTG GTG TTC TCC CCG CTT                                                           348
Pro Pro Pro Tyr Arg Ser Arg Glu Ser Leu Val Phe Ser Pro Leu
         75                  80                      85

TTT CCT CAC GTG GAG AAT GGC ACC CAA CAG TCT TAC GAT TGC CTA                                                           396
Phe Pro His Val Glu Asn Gly Thr Gln Gln Ser Tyr Asp Cys Leu
         90                  95                      100

GAC TGC GCT TAT GAT GGA ATC ATT CAC AGA CTT CAG CTG GCT TTT CTA AGA                                                   444
Asp Cys Ala Tyr Asp Gly Ile Ile His Arg Leu Gln Leu Ala Phe Leu Arg
105                     110                  115

ATT CGC AAA TGC TGT GTA CCG GCT TTA ATT CTT TTT GGT ATT CTC                                                           492
Ile Arg Lys Cys Cys Val Pro Ala Phe Leu Ile Leu Phe Gly Ile Leu
120                     125                  130                  135
```

FIG._6B-1

```
ACC CTT ACT GCT GTC GTG GTC GCC ATT GTT GCC GTT TTT CCC GAG GAA    540
Thr Leu Thr Ala Val Val Val Ala Ile Val Ala Val Phe Pro Glu Glu
                140                 145                 150

CCT CCC AAC TCA ACT ACA TGA                                        561
Pro Pro Asn Ser Thr Thr ***
                155
```

FIG._6B-2

```
                         10              20              30              40              50
ORFS/L (Dumas)    -19   ................A GAGTCGGGGG TGACGGAGTC CCCTCCTTTT    31
M13 S/L C3        -21   .................. .AGTCGGGGG TGACGGAGTC CCCTCCTTTT    29
pV21S             -16   ...............GTCA GAGTCGGGGG TGACGGAGTC CCCTCCTTTT    34
pV21J             -69   .......... .......... .......... .......... ..........   -20
pV4L             -226   .......... .......... .......... .......... ..........  -177
ORFS/L (Oka)      -69   .......... .......... .......... .......... ..........   -20

60              70              80              90              100
ORFS/L (Dumas)     32   CTCGTGAGCG CCACTGGCGC GCGGACTGTT TGTTG---T  TAATAAAAGC    81
M13 S/L C3         30   CTCGTGAGC- -CACTGGCGC GCGGACTGTT TGTTGTTTGT TAATAAAAGC    79
pV21S              35   CTCGTGAGCG CCACTGGCGC GCGGACTGTT TGTTGTTTGT TAATAAAAGC    84
pV21J             -19   .......... .......... .......G  TGTTGTTTGT TAATAAAAGC    31
pV4L             -176   .......... .......... .......... .......... ..........  -127
ORFS/L (Oka)      -19   .......... .......... .......G  GCGGACTGTT TGTTGTTTGT TAATAAAAGC  31

110             120             130             140             150
ORFS/L (Dumas)     82   GGAACGGTTT TTATGAAAAA AGTGTCTGTC TGTCTGTGCG GGCGGGGCGAC  131
M13 S/L C3         80   GGAACGGTTT TTATGAAAAA AGTGTCTGTC TGTCTGTGCG GGCGGGGCGAC  129
pV21S              85   GGAACGGTTT TTATGAAAAA AGTGTCTGTC TGTCTGTGCG GGCGGGGCGAC  134
pV21J              32   .......... .......... AGTGTCTGTC TGTCTGTGCG NGCGGGGCGAC   81
pV4L             -126   .......... .......... .......... .......... ..........   -77
ORFS/L (Oka)       32   GGAACGGTTT TTATGAAAAA AGTGTCTGTC TGTCTGTGCG GGCGGGGCGAC   81

160             170             180             190             200
ORFS/L (Dumas)    132   GGGCGGGGCTG GTCGGACCCC CCCCGAAAA TAACCCCCCC CGGTTTTCTG   181
M13 S/L C3        130   GGGCGGGGCTG GTCGGACCCC CCCC-GAAAA TAACCCCCCC C-GGTTTTCTG   179
pV21S             135   GGGCGGGGCTG GTCGGACCCC CCCC-GAAAA TAACCCCCCC C-GGTTTTCTG   184
pV21J              82   GGVCGGGGCTG GTCGGACCCC CCCC-GAAAA TAACCCCCCC C-GGTTTTCTG   131
pV4L              -76   .......... .......... .......... .......... ..........   -27
ORFS/L (Oka)       82   GGVCGGGGCTG GTCGGACCCC CCCC-GAAAA TAACCCCCCC C-GGTTTTCTG   131
```

FIG._7A

```
              210        220        230        240        250
ORFS/L(Dumas) 182 GGCGCCCGGC GGACCCCGGG AGAGG-AGGC CAGCCCTCTC GCGGCCCCCT 231
M13 S/L C3    180 GGCGCCCGGC GGACCCCGGG AGAGG-AGGC CAGCCCTCTC GCGGCCCCCT 229
pV21S         185 GGCGCCCGGC GGACCCCGGG AGGG--GGCC CAGCCCTCTC GCGGCCCCCT 234
pV21J         132 GGCGCCCGGC GGACCCCGGG GGGGG..... .......... .......... 181
pV4L          -26 .......... .......... ..GGCC..... .......... .......... 24
ORFS/L(Oka)   132 GGCGCCCGGC GGACCCCGGG GGGGGGGGCC CAGCCCTCTC GCGGCCCCCT 181

260        270        280        290        300
ORFS/L(Dumas) 232 CGAGAGAGAA AAAAAAAAGC GACCCCACCT CCCCGCGCGT TTGCGGGGCG 281
M13 S/L C3    230 CGAGAGAGAA AAAAAAAAGC GACCCCACCT CCCCGCGCGT TTGCGGGGCG 279
pV21S         235 .......... .......... .......... .......... .......... 284
pV21J         182 CGAGAGAGAA AAAAAAAAGC GACCCCACCT CCCCGCGCGT TTGCGGGGCG 231
pV21J          25 CGAGAGAGAA AAAAAAAAGC GACCCCACCT CHYCGCGCGT TTG....... 74
pV4L          182 CGAGAGAGAA AAAAAAAAGC GACCCCACCT CCCCGCGCGT TTGCGGGGCG 231

310        320        330        340        350
ORFS/L(Dumas) 282 ACCATCGGGG GGGATGGGAT TTTTTGCCGG GAAACCCCCC CCCGCCAGCC 331
M13 S/L C3    280 ACCATCGGGG GGGATGGGAT TTTTTGCCGG GAAACCCCCC CC-GCCAGCC 329
pV21S         285 .......... .......... .......... .......... .......... 334
pV21J         232 ACCATCGGGG GGGATGGGAT TTTTTGCCGG GAAACCCCCC CC-GCCAGCC 281
pV4L           75 ACCATCGGGG .......... .......... .......... .......... 124
ORFS/L(Oka)   232 ACCATCGGGG GGGATGGGAT TTTTTGCCGG GAAACCCCCC CC-GCCAGCC 281

360        370        380        390        400
ORFS/L(Dumas) 332 TTTAACAAAA CCCGCGCCTT TTGCGTCCAC CCCTCGTTTA CTGCTCGGAT 381
M13 S/L C3    330 TTTAACAAAA CCCGCGCCTT TTGCGTCCAC CCCTCGTTTA CTGCTCGGAT 379
pV21S         335 .......... .......... .......... .......... .......... 384
pV21J         282 .......... .......... .......... .......... .......... 331
pV4L          125 TTTAACAAAA CCCGCGCCTT TTGCGTCCAC CCCTCGTTTA CTGCTCGGAT 174
ORFS/L(Oka)   282 TTTAACAAAA CCCGCGCCTT TTGCGTCCAC CCCTCGTTTA CTGCTCGGAT 331
```

FIG._7B

| | | 410 | 420 | 430 | 440 | 450 | |
|---|---|---|---|---|---|---|---|
| ORFS/L (Dumas) | 382 | GGCGACCGTG | CACTACTCCC | GCCGACCTGG | GACCCCGCCG | GTCACCCTCA | 431 |
| M13 S/L C3 | 380 | GGCCACCGTG | CACTACTCCC | GCCGACCTGG | GACCCCGCCG | GTCACCCTCA | 429 |
| pV21S | 385 | .......... | .......... | .......... | .......... | .......... | 434 |
| pV21J | 332 | .......... | .......... | .......... | .......... | .......... | 381 |
| pV4L | 175 | GGCCACCGTG | CACTACTCCC | GCCGACCTGG | GACCCCGCCG | GTCACCCTCA | 224 |
| ORFS/L (Oka) | 332 | GGCCACCGTG | CACTACTCCC | GCCGACCTGG | GACCCCGCCG | GTCACCCTCA | 381 |

| | | 460 | 470 | 480 | 490 | 500 | |
|---|---|---|---|---|---|---|---|
| ORFS/L (Dumas) | 432 | CGTCGTCCCC | CAGCATGGAT | GACGTTGCGA | CCCCCATCCC | CTACCTACCC | 481 |
| M13 S/L C3 | 430 | CGTCGTCCCC | CGGCATGGAT | GACGTTGCGA | CCCCCATTCC | CTACCTACCC | 479 |
| pV21S | 435 | .......... | .......... | .......... | .......... | .......... | 484 |
| pV21J | 382 | .......... | .......... | .......... | .......... | .......... | 431 |
| pV4L | 225 | CGTCGTCCCC | CGGCATGGAT | GACGTTGCGA | CCCCCATTCC | CTACCTACCC | 274 |
| ORFS/L (Oka) | 382 | CGTCGTCCCC | CGGCATGGAT | GACGTTGCGA | CCCCCATTCC | CTACCTACCC | 431 |

| | | 510 | 520 | 530 | 540 | 550 | |
|---|---|---|---|---|---|---|---|
| ORFS/L (Dumas) | 482 | ACATACGCCG | AGGCCGTGGC | AGACGCGCCC | CCCCCTTACA | GAAGCCGCGA | 531 |
| M13 S/L C3 | 480 | ACATACGCCG | AGGCCGTGGC | AGACGCGCCC | CCCCCTTACA | GAAGCCGCGA | 529 |
| pV21S | 485 | .......... | .......... | .......... | .......... | .......... | 534 |
| pV21J | 432 | .......... | .......... | .......... | .......... | .......... | 481 |
| pV4L | 275 | ACATACGCCG | AGGCCGTGGC | AGACGCGCCC | CCCCCTTACA | GAAGCCGCGA | 324 |
| ORFS/L (Oka) | 432 | ACATACGCCG | AGGCCGTGGC | AGACGCGCCC | CCCCCTTACA | GAAGCCGCGA | 481 |

| | | 560 | 570 | 580 | 590 | 600 | |
|---|---|---|---|---|---|---|---|
| ORFS/L (Dumas) | 532 | GAGTCTGGTG | TTCTCCCCGC | CTCTTTTTCC | TCACGTGGAG | AATGGCACCA | 581 |
| M13 S/L C3 | 530 | GAGTCTGGTG | TTCTCCCCGC | CTCTTTTTCC | TCACGTGGAG | AATGGCACCA | 579 |
| pV21S | 535 | .......... | .......... | .......... | .......... | .......... | 584 |
| pV21J | 482 | .......... | .......... | .......... | .......... | .......... | 531 |
| pV4L | 325 | GAGTCTGGTG | TTCTCCCCGC | CTCTTTTTNC | TCACGTGGAG | AATGGCACCA | 374 |
| ORFS/L (Oka) | 482 | GAGTCTGGTG | TTCTCCCCGC | CTCTTTTTNC | TCACGTGGAG | AATGGCACCA | 531 |

FIG._7C

|              |     | 610         | 620         | 630         | 640         | 650         |     |
|---|---|---|---|---|---|---|---|
| ORFS/L (Dumas) | 582 | CCCAACAGTC | TTACGATTGC | CTAGACTGCG | CTTATGATGG | AATCCACAGA | 631 |
| M13 S/L C3 | 580 | CCCAACAGTC | TTACGATTGC | CTAGACTGCG | CTTATGATGG | AATCCACAGA | 629 |
| pV21S | 585 | ........... | ........... | ........... | ........... | ........... | 634 |
| pV21J | 532 | ........... | ........... | ........... | ........... | ........... | 581 |
| pV4L | 375 | CCCAACAGTC | TTACGATTGC | CTAGACTGCG | CTTATGATGG | AATCCACAGA | 424 |
| ORFS/L (Oka) | 532 | CCCAACAGTC | TTACGATTGC | CTAGACTGCG | CTTATGATGG | AATCCACAGA | 581 |

|              |     | 660         | 670         | 680         | 690         | 700         |     |
|---|---|---|---|---|---|---|---|
| ORFS/L (Dumas) | 632 | CTTCAGCTGG | CTTTTCTAAG | AATTCGCAAA | TGCTGTGTAC | CGGCTTTTTT | 681 |
| M13 S/L C3 | 630 | CTTCAGCTGG | CTTTTCTAAG | AATTCGCAAA | TGCTGTGTAC | CGGCTTTTTT | 679 |
| pV21S | 635 | ........... | ........... | ........... | ........... | ........... | 684 |
| pV21J | 582 | ........... | ........... | ........... | ........... | ........... | 631 |
| pV4L | 425 | CTTCAGCTGG | CTTTTCTAAG | AATTCGCAAA | TGCTGTGTAC | CGGCTTTTTT | 474 |
| ORFS/L (Oka) | 582 | CTTCAGCTGG | CTTTTCTAAG | AATTCGCAAA | TGCTGTGTAC | CGGCTTTTTT | 631 |

|              |     | 710         | 720         | 730         | 740         | 750         |     |
|---|---|---|---|---|---|---|---|
| ORFS/L (Dumas) | 682 | AATTCTTTTT | GGTATTCTCA | CCCTTACTGC | TGTCGTGGTC | GCCATTGTTG | 731 |
| M13 S/L C3 | 680 | AATTCTTTTT | GGTATTCTCA | CCCTTACTGC | TGTCGTGGTC | GCCATTGTTG | 729 |
| pV21S | 685 | ........... | ........... | ........... | ........... | ........... | 734 |
| pV21J | 632 | ........... | ........... | ........... | ........... | ........... | 681 |
| pV4L | 475 | AATTCTTTTT | GGTATTCTCA | CCCTTACTGC | TGTCGTGGTC | GCCATTGTTG | 524 |
| ORFS/L (Oka) | 632 | AATTCTTTTT | GGTATTCTCA | CCCTTACTGC | TGTCGTGGTC | GCCATTGTTG | 681 |

|              |     | 760         | 770         | 780         | 790         | 800         |     |
|---|---|---|---|---|---|---|---|
| ORFS/L (Dumas) | 732 | CCGTTTTTCC | CGAGGAACCT | CCCAACTCAA | CTACATGAAA | CTACTGTCCG | 781 |
| M13 S/L C3 | 730 | CCGTTTTTCC | CGAGGAACCT | CCCAACTCAA | CTACATGAAA | CTACTGTCCG | 779 |
| pV21S | 735 | ........... | ........... | ........... | ........... | ........... | 784 |
| pV21J | 682 | ........... | ........... | ........... | ........... | ........... | 731 |
| pV4L | 525 | CCGTTTTTCC | CGAGGAACCT | CCCAACTCAA | CTACATGA.. | ........... | 574 |
| ORFS/L (Oka) | 682 | CCGTTTTTCC | CGAGGAACCT | CCCAACTCAA | CTACATGA.. | ........... | 731 |

FIG._7D

```
                             810       820       830       840       850
ORFS/L (Dumas)   782 GAAGGGGAAG GTATTTATTC TGGCTTGCAG CTTGTCGCGC GTGTATGCAC  831
M13 S/L C3       780 GAAGGG-AAG GTATTTATTC T-GCTTGCAG CTTGTCGCGC GTGTATGCAC  829
pV21S            785 .......... .......... .......... .......... ..........  834
pV21J            732 .......... .......... .......... .......... ..........  781
pV4L             575 .......... .......... .......... .......... ..........  624
ORFS/L (Oka)     732 .......... .......... .......... .......... ..........  781

860       870       880       890       900
ORFS/L (Dumas)   832 AACAAAAGCT ATATATGTCA CCAAAGCCAA CGTCGCCATC TGGAGTACTA  881
M13 S/L C3       830 AACAAAAGCT ATATATGTCA CCAAAGCCAA CGTCGCCATC TGGAGTACTA  879
pV21S            835 .......... .......... .......... .......... ..........  884
pV21J            782 .......... .......... .......... .......... ..........  831
pV4L             625 .......... .......... .......... .......... ..........  674
ORFS/L (Oka)     782 .......... .......... .......... .......... ..........  831

910       920       930       940       950
ORFS/L (Dumas)   882 CACCCAGTAC GTTGCATAAC CTGTCCATTT CGATTTTCAG TTGCGCGGAC  931
M13 S/L C3       880 CACCCAGTAC ATTGCATAAC CTGTCCATTT GCATTTTCAG TTGCGCGGAC  929
pV21S            885 .......... .......... .......... .......... ..........  934
pV21J            832 .......... .......... .......... .......... ..........  881
pV4L             675 .......... .......... .......... .......... ..........  724
ORFS/L (Oka)     832 .......... .......... .......... .......... ..........  881

960       970       980       990      1000
ORFS/L (Dumas)   932 GCCTTTCTCC GGGATCGTGG CCTTGGGACA TCAACCAGTG GAATAAGAAC  981
M13 S/L C3       930 GCCTTTCTCC GGGATCGTGG CCTTGGGACA TCAACCAGTG GAATAAGAAC  979
pV21S            935 .......... .......... .......... .......... ..........  984
pV21J            882 .......... .......... .......... .......... ..........  931
pV4L             725 .......... .......... .......... .......... ..........  774
ORFS/L (Oka)     882 .......... .......... .......... .......... ..........  931
```

FIG._7E

|  |  | 1010 | 1020 | 1030 | 1040 | 1050 |  |
|---|---|---|---|---|---|---|---|
| ORFS/L (Dumas) | 982 | CGCCGGTGGT | CTTGTTTGAA | CGACGAGTGG | CGACGCGTTG | TTCTGCATAA | 1031 |
| M13 S/L C3 | 980 | CGCCGGTGGT | CTTGCCCGAA | CGACGAGTGG | CGACGCGTTG | TTCTGCATAA | 1029 |
| pV21S | 985 | . . . . . . . . . . | . . . . . . . . . . | . . . . . . . . . . | . . . . . . . . . . | . . . . . . . . . . | 1034 |
| pV21J | 932 | . . . . . . . . . . | . . . . . . . . . . | . . . . . . . . . . | . . . . . . . . . . | . . . . . . . . . . | 981 |
| pV4L | 775 | . . . . . . . . . . | . . . . . . . . . . | . . . . . . . . . . | . . . . . . . . . . | . . . . . . . . . . | 824 |
| ORFS/L (Oka) | 932 | . . . . . . . . . . | . . . . . . . . . . | . . . . . . . . . . | . . . . . . . . . . | . . . . . . . . . . | 981 |

|  |  | 1060 | 1070 | 1080 | 1090 | 1100 |  |
|---|---|---|---|---|---|---|---|
| ORFS/L (Dumas) | 1032 | GCTCTGTATG | CTGATACATA | AACACAGAGT | CTGTATCGCT | ATCAGATTCC | 1081 |
| M13 S/L C3 | 1030 | GCTCTGTATG | CTGATACATA | AACACAGAGT | CTGTATCGCT | ATCAGATTCC | 1079 |
| pV21S | 1035 | . . . . . . . . . . | . . . . . . . . . . | . . . . . . . . . . | . . . . . . . . . . | . . . . . . . . . . | 1084 |
| pV21J | 982 | . . . . . . . . . . | . . . . . . . . . . | . . . . . . . . . . | . . . . . . . . . . | . . . . . . . . . . | 1031 |
| pV4L | 825 | . . . . . . . . . . | . . . . . . . . . . | . . . . . . . . . . | . . . . . . . . . . | . . . . . . . . . . | 874 |
| ORFS/L (Oka) | 982 | . . . . . . . . . . | . . . . . . . . . . | . . . . . . . . . . | . . . . . . . . . . | . . . . . . . . . . | 1031 |

|  |  | 1110 | 1120 | 1130 | 1140 | 1150 |  |
|---|---|---|---|---|---|---|---|
| ORFS/L (Dumas) | 1082 | CGAACACCTT | CCGGTACCCC | ATACTCCGAT | ACCCTGGACA | TTGCGGATCC | 1131 |
| M13 S/L C3 | 1080 | CGAACACCTT | CCGGTACCCC | ATACTCCGAT | ACCCTGGACA | TTGCGGATCC | 1129 |
| pV21S | 1085 | . . . . . . . . . . | . . . . . . . . . . | . . . . . . . . . . | . . . . . . . . . . | . . . . . . . . . . | 1134 |
| pV21J | 1032 | . . . . . . . . . . | . . . . . . . . . . | . . . . . . . . . . | . . . . . . . . . . | . . . . . . . . . . | 1081 |
| pV4L | 875 | . . . . . . . . . . | . . . . . . . . . . | . . . . . . . . . . | . . . . . . . . . . | . . . . . . . . . . | 924 |
| ORFS/L (Oka) | 1032 | . . . . . . . . . . | . . . . . . . . . . | . . . . . . . . . . | . . . . . . . . . . | . . . . . . . . . . | 1081 |

FIG._7F

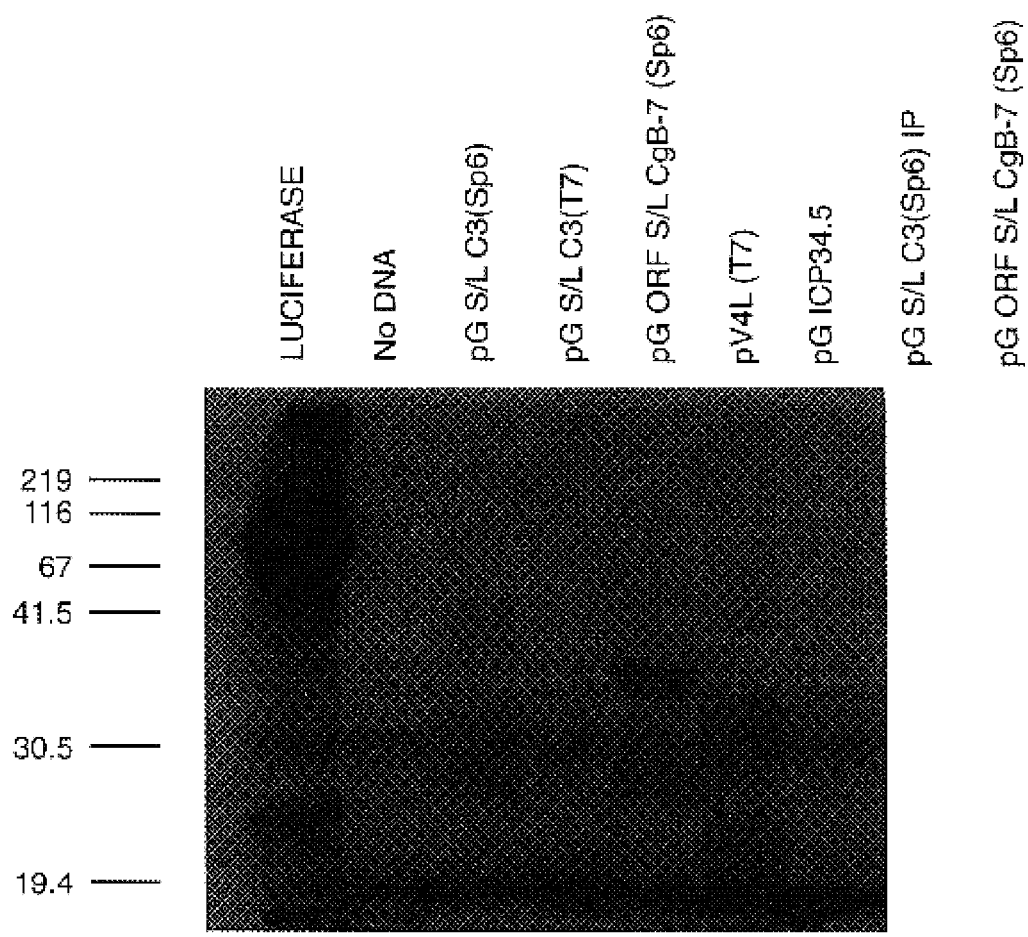
FIG._8

VZV GENE, MUTANT VZV AND IMMUNOGENIC COMPOSITIONS

REFERENCE TO RELATED APPLICATIONS

This is a divisional of application Ser. No. 08/857,534 filed May 16, 1997 and issued as U.S. Pat. No. 6,087,170 on Jul. 11, 2000, which is a continuation application Ser. No. 08/235,406 filed Apr. 28, 1994 and now abandoned.

TECHNICAL FIELD

The invention relates to the identification of a novel Varicella-Zoster Virus (hereinafter to be referred to as VZV) gene. It also relates to methods of making and to novel immunogenic compositions comprising VZV, modified by the modification or deletion of this novel gene and to methods inducing an immune response in a host organism by administration of such immunogenic compositions.

BACKGROUND

Varicella-Zoster Virus, a member of the herpes virus family, causes chicken pox as a primary infection and shingles as a secondary infection. Chicken pox is a common disease of children that is highly contagious but usually not life threatening. In adults chicken pox can pose a more serious medical threat. Shingles occurs after primary infection with the vaccine or the wild type virus. After the primary infection, the virus travels to the trigeminal or thoracic (commonly T3-L2) ganglia and lies dormant. Upon reactivation, the virus affects the dermatome supplied by the corresponding ganglia. Both of these diseases are widespread, with 3–4 million varicella and 850,000 zoster cases in the U.S. per year, and costs $700 million per year in the U.S. in treatment and lost work costs.

Chemotherapy is available to combat VZV infections. Acyclovir chemotherapy halts the progression of disease by acting as a substrate for herpes pyrimidine deoxyribonucleotide kinase. The kinase phosphorylates Acyclovir, and the phosphorylated Acyclovir is then incorporated into viral DNA, which ultimately leads to DNA chain termination. Although chemotherapy is effective in treating infected patients with varicella or zoster symptoms it does not prevent occurrence of either disease.

An alternative post-infection treatment, VZV-specific immunoglobulin, is available, in addition to chemotherapy, to treat VZV infections. However, this treatment is expensive, affords only a narrow window of therapeutic use and must be quality controlled for HIV contamination.

A live, attenuated vaccine made of VZV derived from the Oka strain of that organism has been developed by Takahashi, M., et al., *Lancet* 1974; 2:1288–90. The vaccine was developed by multiple passage of the virus through a mammalian cell line. It protects against chicken pox in humans. However, zoster infections resulting from Oka replication have been documented in humans vaccinated with the Oka vaccine. Unfortunately, no other vaccines against VZV are currently marketed.

Progress toward developing a VZV vaccine has been stymied because no practical animal model exists for determining vaccination and immune responses and because only low viral yields in culture are currently available. Guinea pigs, and perhaps marmosets, can be used as limited models for VZV studies. Infection can be documented in these animals, although latency and reactivation of the virus has yet to be established. One 6 month old gorilla has been shown to be infected with a VZV indistinguishable from a human strain. Even though the disease closely resembled that of human varicella, the gorilla is an impractical disease model for obvious socio-economic reasons. Although culture yields have been improved somewhat by growing attenuated vaccines in monolayers (see for example PCT Patent Application WO93/24616 published Dec. 9, 1993), higher yields would be even more advantageous. Additionally, deletions in the VZV genome to produce attenuated strains of VZV which would make good candidates for live vaccines have yielded varying results. For example, deletion of the gene encoding ribonucleotide reductase slowed viral growth and increased Acyclovir sensitivity. In contrast, prevention of VZV thymidylate synthetase gene expression failed to affect viral growth rates.

As noted previously, VZV is a member of the herpesvirus family. As such, the 120 kilobase (kb) VZV genome shares some structural homology to herpes simplex virus. Both viruses store their virion DNA as a linear molecule and replicate using circular DNA molecules. The linear order of genes within the each DNA molecule is similar for most genes in both herpes simplex virus and VZV. Each genome contains two unique sequences. $U_L$ (standing for "unique long") comprises about 100 kb and $U_S$ (standing for "unique short") comprises about 5 kb. Each $U_L$ sequence is flanked by a terminal repeat sequence, i.e., a $TR_L$ (or terminal repeat of unique long), and an internal repeat sequence, i.e., an $IR_L$ (internal repeat of unique long). Likewise, each $U_S$ sequence is flanked by a terminal repeat sequence, $TR_S$, and an internal repeat sequence, $IR_S$.

However, VZV and herpes simplex virus display numerous differences in their genomic structure as well. The herpes simplex virus genome contains an extra set of inverted repeats called the "a" sequence, in addition to $TR_L$, $IR_L$, $TR_S$ and $IR_S$ sequences. The a sequences are located at both genomic termini, as well as at the junction of the L and S components. The VZV $TR_L$ and $IR_L$ sequences are very short (88 base pairs) compared to the herpes simplex virus $TR_L$ and $IR_L$ sequences (8000 base pairs). Another difference is that there is an origin of DNA replication at the approximate center of the $U_L$ sequence in herpes simplex virus. There is no such structure in VZV. The functional and evolutionary significance of the differences between the repeat regions flanking the UL region in herpes simplex virus and the repeat regions flanking the $U_L$ region in VZV is unknown.

Four different genomic isomers, composed of Par (Parental) and inverted (Inv) forms of the $U_L$ and $U_S$ repeat sequences, exist in the VZV genome: $U_L$-Par/$U_S$-Par, $U_L$-Par/$U_S$-Inv, $U_L$-Inv/$U_S$-Par, and $U_L$-Inv/$U_S$-Inv. The four isomers are not randomly distributed. Two isomers ($U_L$-Par/$U_S$-Par and $U_L$-Par/$U_S$-Inv) account for 95 % of the packaged DNA and the remaining two isomers ($U_L$Inv/$U_S$-Par and $U_L$-Inv/$U_S$-Inv) account for 5 % of the packaged DNA, as shown in FIG. 1.

The VZV genome contains 80 possible open reading frames (hereinafter abbreviated as ORF or ORFs), although fewer genes, approximately 70, are thought to encode gene products used in the viral replication cycle. The ORF's of VZV are based on ORF criteria from Davison, A. J. and Scott, J. E., *Journal of General Virology* (1983); 64:1811–184 (ORFs with a methionine initiation site and at least 150 amino acids or ORFs with a TATA box, no overlap with other ORFs and good codon usage). Little is known about the function of the approximately twenty known VZV gene products. The novel gene identified herein was not detected by Davison & Scott type ORF criteria.

Some of the VZV gene products lacking a demonstrated function show nucleic acid or amino acid sequence homology to herpes simplex virus genes of known function. As used herein, "homolog" or "homologous" refers solely to nucleic acid or protein sequence homology between two sequences from different organisms, and does not encompass any functional similarity. About 62 of the known VZV genes have homologs in the herpes simplex virus genome. Five known VZV genes have no homologs in the herpes simplex virus genome. Homologs are traditionally determined using computer sequence analysis methods or using nucleotide probing of nucleotide sequences, methods that require a level of sequence homology sufficient to allow recognition of homologs above background. The novel ORFS/L gene disclosed herein for the first time had not been previously detected using either of the traditional methods. Surprisingly, it has been found that this novel gene is actually a positional homolog of the $\gamma_1 34.5$ gene of herpes simplex. It apparently previously escaped detection because it lacks a typical TATA consensus element upstream of its open reading frame, it has an unusual and unexpected gene structure and it is located in an unexpected location of the VZV genome.

RELEVANT BACKGROUND LITERATURE

The role of herpes simplex virus $\gamma_1 34.5$ gene in neurovirulence and growth was disclosed in *Science;* 250:1262–1266 (1990), "Mapping of Herpes Simplex Virus-1 Nuro-virulence to $\gamma_1 34.5$, a gene Nonessential for Growth in Culture" by J. Chou, E. R. Kern, R. J. Whitley, and B. Roizman.

The existence of a herpes simplex virus gene product near the internal repeat region of herpes simplex virus genome was disclosed in the *Journal of Virology.* 57:629–637 (1986), "The Terminal a Sequence of the Herpes Simplex Virus genome contains the Promoter of a Gene Located in the Repeat Sequences of the L Component" by J. Chou and B. Roizman.

It has been disclosed that herpes simplex viral mutants, lacking a functional $\gamma_1 34.5$ gene, expressed early proteins, but viral DNA synthesis resulted in the cessation of viral protein synthesis. *Proc. Natl. Acad. of Sci. USA.* 89:3266–3270 (1992), "The $\gamma_1 34.5$ gene of herpes simplex virus 1 precludes . . . " by J. Chou and B. Roizman.

It has been disclosed that the Oka strain of VZV can be reconstructed using overlapping cosmid clones and that mutants, lacking a functional thymidylate synthetase gene, grew at a rate similar to the wild type virus. *Pro. Natl. Acad. of Sci. USA.* 90:7376–7380 (1993), "Generation of Varicefla-Zoster Virus (VZV) and viral mutants from cosmid DNAs: . . . " by J. L. Cohen and K. E. Seidel.

The introduction of a stop codon into the thymidylate synthetase gene resulted in the lack of thymidylate synthetase protein expression without affecting viral growth rates or Acyclovir sensitivity, as disclosed in *XVII International Herpesvirus Workshop Abstract* 1993, "Generation of Varicella-Zoster Virus and Viral Mutants from Cosmic DNA; Thymidylate Synthetase is Not Essential for Replication In Vitro" by Jeffrey I. Cohen and Karen E. Seidel.

For a general review of VZV see *Journal of Virology* 72:475–486 (1991), "Varicella-Zoster Virus" by A. J. Davidson.

The DNA sequence and open reading frames of VZV are disclosed in *Journal of General Virology.* 67:1759–1816 (1986), "The Complete DNA Sequence of VariceUa-Zoster Virus" by A. J. Davison and J. E. Scott.

A bovine Herpes virus gene that is formed during the circularization of a bovine Herpes virus genome was disclosed in the *Journal of Virology;* 67:1328–1333 (1993), "Immediate-Early Transcription over Covalently Joined Genome Ends of Bovine Herpesvirus-1: the circ Gene" by C. Fraefel, et al.

The deletion of VZV ORF's for ribonucleotide reductase slowed viral growth rate, increased Acyclovir sensitivity and reduced plaque size, as disclosed in *XVIII International Herpes Workshop Abstract* 1993, "Production and Characterization of a VZV Mutant Lacking the Large Subunit of Ribonucleotide Reductase" by T. C. Heineman and J. I. Cohen.

The immune response of elderly individuals to the Oka vaccine is discussed in *The Journal of Infectious Diseases;* 166:253–9 (1992), "Immune Response of Elderly Individuals to a Live Attenuated Varicella Vaccine" by Levin, M. J., et al.

The hairless guinea pig model is disclosed in *The Journal of Infectious Diseases;* 163:746–751 (1991), "Varicella in Hairless Guinea Pigs" by Myles, M. G., et al.

Infection of a gorilla by varicella was disclosed in *Journal of Medical Virology,* 23:317–322 (1987), "Varicella in Gorilla" by Myer, M. G. et al.

Lastly, U.S. Pat. No. 4,686,101 (1987); U.S. Pat. No. 4,769,239 (1988), U.S. Pat. No. 4,812,559 (1989) and U.S. Pat. No. 4,952,674 (1990) issued to Ellis and Keller disclose the isolation and cloning of the gC glycoprotein of VZV and their use in vaccines against VZV.

DESCRIPTION OF THE FIGURES

FIG. 1 illustrates the four different isomers of the VZV genome. The isomers are packaged in capsids and differ in the orientation of their unique region sequences. The $U_L$-Par isomers comprise 95% of the packaged DNA. The $U_L$-Inv isomers comprise only 5% of the packaged DNA. The abbreviations associated with each isomer are described in the background section.

FIG. 2 illustrates the general arrangement of three separate reading frames that potentially comprise the ORFS/L gene in Dumas and Oka. The striped region indicates the first open reading frame of the ORFS/L gene. The dark areas, from left to right, represent the second and third reading frames of the ORFS/L gene. The $U_L$-Par isomer in its linear form fails to create a ORFS/L reading frame. The $U_L$-Inv isomer creates a complete ORFS/L reading frame at the internal repeat region. The $U_L$-Par isomer and its concatamic form generates an ORFS/L gene. The circular form of the $U_L$-Par isomer also generates a ORFS/L gene.

FIG. 3 illustrates one possible gene structure of ORFS/L reading frames (based on $U_L$-Inv) used for isolating the ORFS/L gene with the polymerase chain reaction and primers as discussed in Example 2.

FIG. 4 illustrates the 4 overlapping segments of VZV genome cloned into cosmids made in Example 5 and the restriction sites used in those cosmids. VZV genomic DNA was cut into 4 fragments as shown using restriction enzymes Fsp I, Spe I and Pme I. The fragments were cloned into cosmids as discussed in Example 5.

FIGS. 5A and B illustrate the DNA sequence of the ORFS/L gene from Dumas and the corresponding amino acid sequence of the ORFS/L protein encoded by the nucleotide sequences. The DNA sequence comprises either the first and second reading frames or the first and third reading frames as illustrated in FIG. 2. The second and third reading frames are identical in Dumas. The location of the reading frame junction between the second and first ORF is indicated by the slash "|" mark in FIG. 5A.

FIGS. 6A-1 and 2, and 6B-1 and 2, illustrate the DNA sequence of the ORFS/L gene from Oka and the corresponding amino acid sequence of the ORFS/L proteins encoded by the nucleotide sequences. FIG. 6A is the nucleotide and corresponding amino acid sequence of the PCR clone p S/L C3 generated from Oka. FIG. 6B is the nucleotide and corresponding amino acid sequence of the first ORF from the ORFS/L gene generated from a plasmid containing Oka genomic DNA, pV4L. Amino acid "Xxx" denotes one of the following amino acids: proline, threonine, serine, and alanine. The second and third reading frames are nearly identical in Oka and are not shown in FIG. 6B (they are listed as SEQ ID NO:15 and SEQ ID NO:16, respectively). The location of the reading frame junction between the second and first ORF is indicated by the slash "|" mark in FIG. 6A-1.

FIGS. 7A–F illustrate a comparison of the following ORFS/L gene DNA sequences: ORFS/L gene (Dumas) (SEQ ID NO:9), m13 S/L C3 from the ORFS/L gene of Oka (SEQ ID NO:11), pV4L from the ORFS/L gene from genomic Oka DNA (SEQ ID NO:13), pV21J from the ORFS/L gene from genomic Oka DNA (SEQ ID NO:15), pV21S from the ORFS/L gene from genomic Oka DNA (SEQ ID NO:16) and the complete ORFS/L gene from Oka genomic DNA (SEQ ID NO:17). When used in nucleotide sequences, as shown herein, for example in the Figures and sequence listing, "V" denotes A, C or G and not T or U; "H" denotes A, C, T or U and not G; and "Y" denotes C, T or U.

FIG. 8 illustrates the expression of various Oka ORFS/L genes and constructs as discussed in Examples 1, 2, 3 and 5.

SUMMARY OF THE INVENTION

The present invention provides a novel VZV gene, termed Open Reading Frame S/L (abbreviated herein as ORFS/L), not heretofore recognized or known in the art. The new ORFS/L was originally found in the Dumas strain of VZV and comprises two combinations of three previously unknown and unidentified ORFs near the terminal and internal repeat regions of the VZV genome. (The gene's name, ORFS/L, is derived from the observation that the S and L components must be joined to create the open reading frame.) The new ORFS/L has also been identified in the Oka strain of VZV. Prior to the invention, the location and sequence of the ORFS/L eluded detection. The ORFS/L was refractory to discovery due to lack of consensus initiation and polyadenylation signals, its unexpected gene structure and its unusual location in the VZV genome. The invention also provides novel ORFS/L proteins encoded by the gene.

In another aspect the invention provides mutant VZV comprising all or a portion of the VZV genome having a mutation in the ORFS/L gene.

In another aspect the invention provides immunizing compositions comprising such mutant viruses.

In yet another aspect, the invention comprises a method of making such immunizing compositions and also provides other diagnostic and therapeutic uses for the gene and its protein product.

Most desirably, mutant viruses and immunogenic compositions are provided that comprise VZV attenuated with respect to both varicella primary infections and zoster secondary infections. The mutant VZV of this invention comprises VZV in which the gene of the newly identified open reading frames ORFS/L gene are deleted, modified by nucleic acid substitution or by partial deletion of one or more nucleic acids, or by insertion of a codon that terminates translation of the gene. The mutant VZV of this invention may be also used with a deletion or mutation of other non-essential and essential VZV genes. As used here, "mutant VZV" means VZV containing at least a mutation in the ORFS/L gene ("mutation" as used in this specification is defined in the Detailed Description). Such compositions will retain the immunogenic character of VZV but will be unable to exhibit neurovirulence characteristic of the virus.

In accordance with the invention, the ORFS/L gene sequence is altered to create mutant VZV and compositions having immunogenic properties. Alterations include deletion of the entire gene, part of the gene, site specific mutations, and introduction of a translation termination signal into the gene. It is anticipated that the VZV containing the altered gene will lack its normal neuro-virulence but retain its immunogenic character. If the ORFS/L gene is modified in a VZV strain already attenuated for varicella, such as the Oka strain currently approved as a vaccine, it is anticipated that a virus with attenuated characteristics for both varicella and zoster will result. Immunogenic compositions containing such modified strains may result in improved vaccine compositions in which the possibility of causing a latent zoster infection by administration of the VZV vaccine is eliminated.

In addition, the novel ORFS/L gene and its protein product(s) can be used in the study of programmed cell death (apoptosis) and in the preparation of diagnostic assays for VZV infection, as discussed more fully below.

DETAILED DESCRIPTION

A. Introduction

The invention provides a novel VZV gene, termed ORFS/L, not heretofore recognized or known in the art. The invention also provides mutant VZV characterized by having at least one mutation in the ORFS/L gene, a mutation which results in modified or altered production of ORFS/L protein. The invention also provides immunization compositions and methods comprising the mutant VZV of the invention and also provides other diagnostic and therapeutic uses for the gene and its protein product. The new ORFS/L gene was originally found in the Dumas strain of VZV and comprises two combinations of three previously unknown ORFs near the terminal and internal repeat regions of the VZV genome. The new ORFS/L gene has also been identified in the Oka strain of VZV. Details of its sequence and structural characteristics are provided in the Examples below. Briefly, the ORFS/L gene comprises VZV (Dumas) genomic DNA corresponding to a sequence of a first ORF from nucleotides 1 through 562, a second ORF from nucleotides 104,925 through 105,125 and a third ORF from nucleotides 124,772 through 124,884. The ORFS/L gene nucleotide sequence from Dumas encodes a 224 amino acid protein, starting at the first ATG, having a predicted molecular weight for the mature protein of about 24,265 daltons.

Most desirably, mutant VZV and VZV immunogenic compositions including mutant VZV are provided that comprise VZV attenuated with respect to both varicella primary infections and zoster secondary infections. The mutant VZV and VZV immunogenic compositions of this invention comprise VZV in which the gene and in most instances the gene product of ORFS/L gene are modified by deletion, nucleic acid substitution or deletion, or by insertion of a codon that stops translation of the gene, in order to detrimentally affect neurovirulence while retaining the immunogenic character of VZV.

Thus, one aspect of this invention includes isolated DNA and corresponding RNA sequences that encode the ORFS/L proteins. As used herein, "isolated" means substantially free from other nucleotide or polypeptide sequences with which the subject nucleotide sequence or polypeptide sequence is typically found in its native, i.e., endogenous, state. In another aspect, the invention comprises isolated ORFS/L protein.

Another aspect of this invention includes mutant VZV having at least one mutation in the ORFS/L gene. The identification of the ORFS/L gene permits the introduction of defined mutations in the VZV genome. The modified VZV compositions of this invention are characterized by gene mutation or mutations that produce no substantial disease states, diminish the likelihood of reactivation that leads to shingles, stimulate the immune system and replicate in cells of non-neuronal tissue origin.

Yet another aspect of this invention includes diagnostic assays for the detection of VZV strain variants. In brief, such diagnostic assays include the use of ORFS/L fragments as primers for amplifying ORFS/L related nucleic acids in a polymerase chain reaction (PCR), and the use of ORFS/L genes modified with a unique restriction site to act as vaccine markers.

It is anticipated that the invention will enable the production of vaccines that offer advantages over the current VZV vaccine, which can cause shingles post vaccine infection. Due to the unique nature of the ORFS/L gene, the likelihood of developing shingles post administration of the modified VZV immunogenic compositions of the present invention is expected to be much less than the likelihood of developing shingles from currently used vaccines. Vaccines produced in accordance with the invention will have a second advantage over cell passage vaccines for VZV because the degree of attenuation achieved can be predicted and maintained throughout production and the likelihood of reversion is significantly less in the mutant VZV and VZV immunogenic compositions of the present invention as compared with the currently used cell passage VZV vaccine. More specifically, modification or alteration of the novel ORFS/L gene of the present invention results in the introduction of specific, desired and chosen changes in the VZV genome that are not possible using the cell passage vaccines, which contain only nonselective mutations. Such mutation allows for easier identification of individuals infected with wild type VZV and therefore has useful diagnostic applications. More importantly for vaccine production however, it also enables precise measurement of the degree of attenuation introduced by different mutations in the ORSF/L gene.

The mutant VZVs of the present invention stimulate the immune system because sufficient amounts of VZV glycoprotein, which form the basis of the immune system's response to viral infection, are retained in the composition to stimulate an immune response. Mutant VZV compositions of the present invention contain these glycoproteins, which are sufficiently similar to the wild type glycoproteins, to stimulate an immune response because regions of VZV genome encoding such glycoproteins that are known to be important antigens are not altered in the mutant VZV compositions of the present invention.

Mutant VZVs of the present invention comprising mutations, substitutions, additions, deletions or stop codon introductions in the ORFS/L gene still permit efficient viral replication in cells of non-neuronal tissue origin. Approximately, 14 DNA metabolism enzymes are present in the VZV genome. In the mutant VZVs of this invention, these enzymes remain sufficiently similar to their counterparts in the wild type virus so as to maintain efficient replication in non-neuronal tissues. The ORFS/L gene was selected for modification, in part, because it bears no sequence homology to DNA metabolism enzymes, which would potentially affect viral propagation in cells of non-neuronal tissue origin. Accordingly, the mutant VZVs of the present invention retain the immunogenicity of wild type VZV.

B. Mutant VZVs and Immunogenic Compositions

The ORFS/L gene comprises ORFS/L protein coding regions, and ORFS/L noncoding regions. Protein coding regions are delineated by the amino acid sequence encoded by ORFS/L gene. The noncoding regions are delineated by either the transcript size of the ORFS/L gene, regions of homology surrounding ORFS/L gene reading frames, or sequences in the noncoding regions which control the initiation and termination of transcription. As used herein, the term "ORFS/L gene" refers to an ORFS/L gene from any VZV strain, unless as a specific strain is enumerated. For example, "ORFS/L (Dumas)" and "ORFS/L (Oka)" refer to the ORFS/L of the Dumas and Oka strains, respectively. Also as used herein, the term "ORFS/L gene" encompasses the DNA and RNA version of the gene, single stranded or double stranded, and in the sense or antisense orientation. Different strains of VZV ORFS/L genes, whether from recombinant sources, synthesized, or naturally occurring, that are 90% homologous to either the Dumas or Oka ORFS/L gene (as described in FIGS. 5, 6 and/or 7 and SEQ ID NO:9–17) are also considered to be ORFS/L genes or fragments thereof, as defined herein.

Mutant VZVs comprise VZV characterized as containing at least one mutation in the ORFS/L gene that alters the function or the level of expression of the ORFS/L gene product. Such a mutation can include the introduction of a termination signal in the ORFS/L gene, the deletion of all or a part of the coding or noncoding sequence, the introduction of one or more extra nucleotide(s) that changes the reading frame of the gene, and point mutations or site specific deletion or substitution of specific nucleotides using techniques already known in the art. Introduction of a termination signal is accomplished, for instance, using stop sequences in single or multiple reading frames. Mutation in the coding region of the ORFS/L gene comprising single or multiple substitution, insertion or deletion will alter the function of the ORFS/L protein by directly modifying the polypeptide sequence encoded by the ORFS/L nucleotide sequence. Mutations can also be made that do not change the polypeptide sequence but only change the nucleic acid sequence of the ORFS/L gene or substitute degenerate codons for the native codons, in order to change the codon frequency or introduce a restriction enzyme site. The ORFS/L gene can also be modified by mutation of the transcriptional control elements of the gene in order to alter the level of expression of the ORFS/L gene product. Such modification can be accomplished in the foregoing manner using substitutions, insertions or deletions in the nucleotide sequence. As used here, "mutation" includes any of the foregoing modifications in gene structure disclosed herein, including single or multiple point mutations or site specific substitutions or deletions, single or multiple insertions or additions in the nucleotide sequence, deletions or substitution of all or a substantial part of the nucleotide sequence or single or multiple substitution or deletion of part of the nucleotide sequence of the ORFS/L gene.

With respect to mutations that comprise deletions in the gene, the length of the deletion, whether single or multiple, will preferably total at least 30 bases in length, more preferably at least 75 bases, and most preferably at least 300 bases. Deletions of nucleotides that encode amino acids conserved between VZV strains are preferred. The portion of the ORFS/L gene remaining after deletion is one embodiment of a fragment of the ORFS/L gene discussed herein. Also, preferred are deletions in the coding region of the ORFS/L gene nucleic acid sequence that comprise deletions of at least one amino acid selected from the group consisting of Glutamine, Asparagine, Arginine, Lysine, and Proline. More preferably, the deleted ORFS/L nucleotides encode at least two amino acids selected from that group. For example, a preferred mutant VZV composition of the present invention might include VZV having a nucleic acid sequence deletion from the ORFS/L gene encoding one Glutamine and one Argimnie. Most preferable are mutant VZV compositions comprising VZV characterized by having deletions comprising a portion of the ORFS/L nucleotide sequence that encode at least three proline residues With respect to mutations that comprise one or more alterations or deletions in the coding region of the ORFS/L gene, mutations that result in an amino acid sequence that is at least 80% homologous to the wild type ORFS/L amino acid sequence are preferred, and mutations that result in amino acid sequences that are 90% homologous are especially preferred. Mutant VZV compositions in which the ORFS/L gene contains mutations in that portion of the gene located in the unique long region of the VZV genome are especially preferred.

In some embodiments, mutations of the ORFS/L gene will alter the ability of the mutant VZV to grow in cells of neuronal tissue origin by decreasing or preventing propagation in cells of neuronal tissue origin. Preferably an ORFS/L gene mutation will reduce viral growth in cells of neuronal tissue origin by at least 20%, more preferably by at least 50% and most preferably by at least 75%. The test for attenuated neurovirulence and growth in cells from non-neuronal tissue is described in Example 10.

Since a mutation introduced into the ORFS/L gene could result in reduced production of the virus, it may be required that the gene product of the ORFS/L gene be supplied in trans to achieve good replication of the modified VZV in culture for commercial production. Should ORFS/L prove to be essential for growth of commercial quantities of VZV in culture, it will be desirable to derive a cell line that can support replication of the recombinant virus. The ORFS/L coding region, will be placed under transcriptional control of a promoter such as the CMV (cytomeglovirus) major immediate early promoter, the SV40 early promoter or some other viral or cellular promoter that generates adequate levels of expression, as discussed herein. A cell line, such as VERO, will be cotransfected with a plasmid containing the promoter driven ORFS/L gene and a plasmid containing a drug resistance gene. The cells will be selected for growth in the presence of the appropriate antibiotic. For example, if the drug resistance gene is neo, the cells will be selected for growth in the presence of G418. Resistant cell lines will then be tested for their ability to support the growth of the recombinant virus by cotransfecting the overlapping cosmids containing the appropriate mutation and determining whether infectious virus was formed. These cell lines will then be used to generate large amounts of the recombinant virus. More subtle changes in the ORFS/L gene, if required to facilitate vaccine production, are attained using alterations of the transcription promotion region.

A mutant VZV can be made by isolating the native ORFS/L gene in a wild type virus strain or any recombinant VZV and incorporating the desired mutation into the ORFS/L gene as discussed herein. Mutant VZV can also be produced using VZV with additional modifications in other essential and non-essential genes, such as, but not limited to, the uracil-DNA glycosylase or thymidylate synthetase genes. The modified gene can then be reincorporated into a viral genome or virus using techniques known in the art, such as homologous recombination using flanking sequences; or the modified gene can be reincorporated into a viral genome or virus using cosmid techniques discussed herein and in the art. Because the second and third ORF's of the ORFS/L gene are located in the $IR_S/IR_L$ and TRs repeat sequences, respectively, any intended mutation of or within these regions will require that both copies of the sequence present in the wild type virus are deleted or altered. Alternatively, a mutant VZV may be made comprising a modification of the first ORF such that duplicative mutation is unnecessary in the second and third ORF's. Because 474 nucleotides of the first ORF (corresponding to nucleotides in the region of 1 through 562 (first ORF) of the VZV (Dumas) genomic sequence encoding ORFS/L) are not repeated, mutations in the first ORF of the sequence the ORFS/L gene are preferred.

Alternatively, whole wild type VZV need not be used as starting material. Defective VZV vectors can be used. Such vectors may be constructed using known techniques. Exemplary defective vectors, which typically contain DNA or RNA sequences including the viral packaging site, the origin of replication, a promoter sequence to direct transcription and a translation limitation sequence, a polyadenylation sequence to terminate transcription and a selectable marker or reporter sequence to permit selection of the vector. Such defective vectors constructed from Herpes simplex 1 sequences are described in PCT Patent Publications WO90/09441 published Aug. 23, 1990; WO 92/07945 publishes May 14, 1992 and in EP Patent publication 0 453 242 published Oct. 23, 1991 relating the teachings of which we herein incorporates by reference. Exemplary vectors using poxvirus sequences are disclosed in EP Patent 0 110 385 published Jun. 13, 1984.

Yet another alternative is to incorporate VZV DNA sequences lacking ORFS/L sequences into a non-VZV viral vector or genome, such as, herpes simplex virus. As used here, viral vector means a nucleic acid molecule in which a gene sequence to be transferred is fused to a subset of viral sequences that are capable of expressing the gene at some point in the viral lifecycle.

VZV DNA sequences lacking ORF/L sequences are inserted into non-VZV viral vectors or genomes using the cosmid techniques discussed herein to reconstruct VZV from four cosmids, with overlapping VZV DNA fragments. When a non-VZV viral vector or genome or chimeric genome is desired at least one, or part of one, of the four fragments used in the cosmid technique to reconstruct a VZV virus will be a non-VZV, viral genome fragment.

C. Production of Mutant VZV

VZV with a mutant or wild type ORFS/Ls will be grown in tissue culture cells. For experiments with mammals, not including humans, cells such as human foreskin fibroblasts (HF), human neuroblastoma cells (SK-N-SH), human or murine neuroblastoma cells or cell lines, MRC-5 cells, VERO cells, or MeWO cells will be used to propagate the virus. Mutant VZV virus will be harvested from cultures of these cells described. The isolated mutant virus will then be further studied for its ability to elicit an immune response and/or provide protection against VZV infection.

Mutant VZV for use in humans will be produced from an FDA approved cell line in large scale amounts. Such cells include MRC-5 or WI-38 cells (both are primary human diploid fibroblasts) or VERO cells. The mutant VZV will be generated in the production cell line either by transfection using overlapping VZV fragments from four cosmids as discussed below or transfection of viral DNA or capsids prepared from mutant VZV isolated from another cell line. Either method of transfection will prevent the contamination of FDA approved cells with adventitious agents or contaminants from a non-qualified cell line.

A mutant VZV produced from the above cell lines will be used to infect progressively larger flasks of tissue culture cells. Infected cells will be used as subsequent inoculums. Viable infected tissue culture cells are removed from the tissue culture vessels using trypsin and added to a 1 to 100 fold (or more) excess of uninfected cells to accomplish progressively larger inoculations. Once an optimal yield is obtained the mutuant VZV will be harvested from the tissue culture cells. This process can be repeated until a large scale production is achieved. Infected cells will be removed from the tissue culture vessel and disrupted using for example, sonication, dounce homogenization or some combination of the above. The viruses are then isolated from cellular material using centrifugation techniques known in the art. Once the virus is isolated a stabilizing agent is added, such as a carbohydrate or carbohydrate derivative and the virus is then aliquoted and lyophilized.

D. VZV Vaccines and Immunogenic Compositions

VZV vaccines or immunogenic compositions can be administered to subjects to prevent VZV infections. Both primary and secondary infections can be prevented. The vaccine prevents varicella infections by stimulating the immune system with an attenuated virus incapable of fully manifesting the disease. The vaccine prevents zoster infections because changes in the ORFS/L gene interfere with the virus' ability to reactivate.

The VZV vaccines described in this invention are administered to prevent the acquisition of chicken pox or shingles by inducing immunity in subjects not previously exposed to the virus in recipients of the vaccine or to subjects previously exposed to the virus in order to prevent zoster. The therapeutic administration of the vaccine should help to reduce the possibility of developing shingles in adult vaccines due to a VZV strain they acquired earlier than vaccination. The vaccine can be used in mammals, preferably primates, such as monkey or gorilla, and most preferably in humans.

A major advantage of the VZV vaccine provided herein is that it will not reactivate to cause shingles. VZV(Oka) has been documented to reactivate and cause shingles in certain populations. Reactivation is also known to occur in the native herpes simplex virus. However, in herpes simplex virus lacking the $\gamma_1$ 34.5 gene linked to reactivation has been demonstrably reduced in animal models. By deleting or modifying the ORFS/L gene in VZV it is anticipated that a similar reduction in reactivation frequency will result. Two reading frames of the VZV ORFS/L (Dumas) gene, the first (VZV genomic sequence 1–562) and second (VZV genomic sequence 105,125–105,013 appended to 105,012–104,925) share similar positions to the two reading frames of herpes simplex virus $\gamma_1$ 34.5 gene in their respective genomes, although the ORFS/L gene and the $\gamma_1$ 34.5 gene are not considered structural homologs. In the VZV genome, corresponding parts of the ORFS/L gene are located just proximal to the $U_L$ 5' repeat region and in the $IR_L$ regions, while in the $\gamma_1 34.5$ gene is located at the $U_L$ 3' and 5' repeat region of herpes simplex virus-1. Because the $\gamma_1 34.5$ gene has been linked to a reduction of herpes simplex virus-1 reactivation in animal models, mutations to the ORFS/L gene from VZV will generate a vaccine disabled in its ability to reactivate and cause shingles.

VZV(Oka) will serve as the parent strain due to its ability to stimulate an immune response and protect subjects from getting chicken pox. The vaccines derived using a mutated ORFS/L gene from an Oka strain will be unable to cause shingles, unlike Oka. Different VZV strains, other than Oka, can be used with a disabled ORFS/L gene to generate an attenuated virus, such as: RIT/Oka, Merck/Oka, Ellen, EF, Webster A, Yamada, Izawa, Tsuchiyama, Watanabe, Wada, Terada, Kawaguchi, Inoue, SY, Scott, KMcC, AW, H-551, CP5,262, 80–2, 1294, 6050 and delta (Simian varicella virus). Clinical isolates with better growth or immune stimulation properties are preferred strains for making vaccines with the invention.

To make a VZV vaccine or immunogenic composition a modified ORFS/L gene will be produced in a VZV virus as discussed herein. The effectiveness of the vaccine in preventing Varicella infections will be measured in humans. Humans will be first inoculated with PFU's ranging from 100–20,000 PFU of mutant VZV per inoculation. PFUs are measured as discussed herein. After the first inoculation, a second booster injection of similar or increased dosage usually will be given. Subjects will be exposed to wildtype VZV after the first or second inoculation and the occurrence of varicella infections observed. Potential side effects of the vaccine will be monitored in volunteer adults previously exposed to VZV, before inoculating subjects that have not ever developed varicella infections. Attenuated virus is used without an adjuvant and with a physiologically suitable carrier.

As is known in the art and discussed herein, the modified DNA, in this case ORFS/L DNA containing mutations in the sequence, is inserted into the viral genome using, for example, homologous recombination techniques. The insertion is generally made into a gene which is non-essential in nature, for example, the thymidine kinase gene (tk), which also provides a selectable marker. Plasmid shuttle vectors that greatly facilitate the construction of recombinant viruses have been described (see, for example, Mackett, et al. (1984); Chakrabarti, et al. (1985); Moss (1987)). Expression of the heterologous polypeptide then occurs in cells or individuals which are immunized with the live recombinant virus.

E. Diagnostic Assays and Use as a Vaccine Marker

The novel ORFS/L gene of the present invention can be used in diagnostic assays to detect VZV in a sample, to detect ORFS/L-like genes and to detect strain differences among ORFS/L genes using either chemically synthesized or recombinant ORFS/L gene fragment. Additionally, the novel ORFS/L gene can be used as a vaccine marker to differentiate between an individual or sample infected with or containing wild type VZV and an individual or sample infected with or containing a VZV vaccine, i.e., a live attenuated VZV vaccine currently in use such as the Oka vaccine. In yet another embodiment, fragments of the ORFS/L gene can also be linked to secondary nucleic acids with sequences that either bind a solid support or other detection probes for use in diagnostic assays.

In one aspect of the invention fragments of the ORFS/L gene comprising at least between 10 and 20 nucleotides can be used as primers to amplify nucleic acids using polymerase chain reaction (PCR) methods well known in the art and as probes in nucleic acid hybridization assays to detect target genetic material such as VZV DNA in clinical specimens (with or without PCR). See for example, U.S. Pat. Nos. 4,683,202; 4,683,195; 5,091,310; 5,008,182 and 5,168,039. In an exemplary assay, a conserved region of the ORFS/L gene among virus variants is selected, for example nucleotides 70 through 800, as shown in FIG. 6a, as the sequence to be amplified and detected in the diagnostic assay. Oligonucleotide primers at least substantially complementary to (but preferably identical with) the sequence to be amplified are constructed and a sample suspected of containing a VZV nucleic acid sequence to be detected is treated with primers for each strand of VZV nucleic acid sequence to be detected, four different deoxynucleotide triphosphates and a polymerization agent under appropriate hybridization conditions such that an extension product of each primer is synthesized that is complementary to the VZV nucleic acid sequences suspected in the sample, which extension products synthesized from one primer, when separated from its complement can serve as a template for synthesis of the extension product of the other primer in a polymerase chain reaction. After amplification, the product of the PCR can be detected by the addition of a labeled probe, likewise constructed from the ORFS/L sequence, capable of hybridizing with the amplified sequence as is well known in the art. See, e.g. U.S. Pat. No. 5,008,182. In another embodiment the ORFS/L gene probes or primers can be used in a vaccine marker assay to detect a vaccine or wild type infection. In this assay regions of the ORFS/L gene with the least homology between the vaccine and the wild type are preferred for use as primers or probes. Alternatively, introduction of a restriction site into the ORFS/L gene will provide an ORFS/L gene vaccine marker that can be used with PCR fragments to detect such differences in a restriction digest. Such procedures and techniques for detecting sequence variants, such as, point mutations with the expected location or configuration of the mutation, are known, are already known in the art and have been applied in the detection of sickle cell anemia, hemoglobin C disease, diabetes and other diseases and conditions as disclosed in U.S. Pat. No. 5,137,806. These methods are readily applied by one skilled in the art to detect and differentiate between wild type and vaccine infections in VZV.

In another embodiment the ORFS/L gene can be used in its entirety or as fragments to detect the presence of ORFS/L gene, related genes, or ORFS/L gene transcription products in cells, tissues, samples and the like using hybridization probe techniques known in the art or in conjunction with one of the methods discussed herein. When used as a hybridization probe, fragments of the ORFS/L gene are preferably 50–200 nucleotides long, whole preferably 100–300 nucleotides long and most preferably greater than 300 nucleotides long.

F. ORFS/L Vectors and Chimeric VZV Virus Production

The ORFS/L gene can be expressed in different vectors using different techniques known in the art resulting in the generation of chimeric VZV virus. Useful and known techniques include marker transfer or homologous recombination, direct in vitro ligation, defective vector technology and amplicon generation (see, e.g., Frenkel, N. et al., *Gene Transfer and Cancer*, edited by M. L. Pearson and N. L. Sternberg(1984), Kwong, A. D. and Frenkel, *Virology* 142, 421–425(1985); U.S. Patent (Ser. No. 07/923,015 by Roizman). Vectors used in such techniques include cosmids, plasmids, and infective or defective viruses. Such vectors are known in the art. (A cosmid as used herein is a plasmid containing a lambda bacteriophage cos site. The cos site is the cis signal for packaging lambda DNA. Therefore, a cosmid, unlike a plasmid, can be packaged with high efficiency into a lambda head in vitro. This technique allows cloning of very large (30–45 kbp) fragments of DNA.) The vectors can be either single stranded or double stranded and made of either DNA or RNA.

Generally, the ORFS/L gene is inserted into the vector alone or linked to other VZV genomic DNA. In direct in vitro ligation applications, the isolated ORFS/L gene alone is used. In homologous recombination and marker transfer flanking nucleic acid sequences are required to effect transfer of the ORFS/L sequence into a VZV viral genome. For ORFS/L gene use in viral complementation using cosmids and other vectors discussed herein the ORFS/L gene (or a fragment of the gene) in a vector is preferably operatively linked to at least 1 kb of VZV genomic nucleic acid and more preferably at least 5 kb of VZV nucleic acid. The VZV genomic nucleic acid can be on one side or both sides of the ORFS/L gene. If only a specific region of the ORFS/L gene is to be used to generate a mutant VZV virus, an open reading frame or fragment of the ORFS/L gene is inserted into a vector. Preferably, the ORFS/L gene, operatively linked to a vector, has a mutation.

G. ORFS/L Protein

Another aspect of the invention includes the isolated ORFS/L protein encoded by the ORFS/L gene DNA sequence as taught herein. The ORFS/L protein can be used to study and modify the life cycle of VZV because the ORFS/L gene uniquely forms a complete gene during two time specific periods in the VZV viral life cycle, during concatamer DNA formation and during circular DNA formation. The novel VZV ORFS/L gene is also implicated in cell apoptosis by virtue of its similarity with the $\gamma_1$ 34.5 gene of herpes simplex virus. This similarity makes ORFS/L protein a useful tool and therapeutic for studying and treating degenative diseases of the central nervous system caused by cell death.

The ORFS/L proteins comprise a Dumas protein with 224 amino acids (24,265 daltons) as shown in FIG. 5, an Oka protein with 223 amino acids (23,775 daltons) as shown in FIG. 6a and an Oka protein with 157 amino acids (17,123 daltons) as shown in FIG. 6b. The term "ORFS/L protein," refers to the sequences shown in FIGS. 5, 6a and 6b, and the sequence listing, unless a specific strain is indicated. The term "ORFS/L protein" as used herein refers to an ORFS/L protein from any strain of VZV and to proteins that are at least 90% homologous to the ORFS/L amino acid sequences show in FIGS. 5 and 6. The ORFS/L protein can be modified to affect VZV life cycle or apoptosis by deletion, insertion and substitution into the ORFS/L gene DNA sequence, as discussed herein, or by chemical synthesis of different amino acid sequence or by chemical modification. Truncated ORFS/L proteins can be formed by deletion of a portion of the ORFS/L DNA sequence or the introduction of termination signal(s) into the ORFS/L gene DNA sequence. Preferred deletions to the ORFS/L protein correspond to deleted amino acid sequence or sequences that contain at least one amino acid selected from the group consisting of Glu, Asp, Arg, Lys, Cys and Pro. More preferably at the deleted amino acid sequence or sequences contain at least two amino acids selected from the group consisting of Glu, Asp, Arg, Lys, Cys and Pro. More preferably the deleted amino acid sequence or sequences contain at least two prolines. Also, preferred are mutations related to mutant VZV discussed herein, where ORFS/L protein mutations prevent shingles or decrease viral propagation in cells of neuronal tissue origin.

Other mutations of the ORFS/L protein useful in modifying VZV life cycle or apoptopsis include, but are not limited to, modification of cAMP phosphorylation (Arg/Lys-Arg/Lys-X-X-Asp/Glu) and/or, myristylization sites (Glycine-XI-X2-X2-Ser/Thr-X-X-Asp/Glu; where X1 is not Glu,Asp,Arg, Lys, His Pro, Phe, Tyr, Trp, where X2 is any amino acid and where X3 is not Pro), or modification of the PKC phosphorylation sites (Ser/Thr-X-Arg/Lys) and/or N-linked glycosylation sites (Asn-X-Ser/Thr; where X is not Pro).

The ORFS/L gene or fragments thereof can be expressed in a mammalian, insect, or microorganism host. The polynucleotide encoding ORFS/L genes are inserted into a suitable expression vector compatible with the type of host cell employed and is operably linked to the control elements within that vector. Vector construction employs techniques which are known in the art. Site-specific DNA cleavage involved in such construction is performed by treating with suitable restriction enzymes under conditions which generally are specified by the manufacturer of these commercially available enzymes. A suitable expression vector is one that is compatible with the desired function (e.g., transient expression, long term expression, integration, replication, amplification) and in which the control elements are compatible with the host cell.

Mammalian Cell Expression

Vectors suitable for replication in mammalian cells are known in the art, and can include viral replicons, or sequences that ensure integration of the sequence encoding ORFS/L into the host genome. Exemplary vectors include those derived from simian virus SV40, retroviruses, bovine papilloma virus, vaccinia virus, and adenovirus.

Such suitable mammalian expression vectors contain a promoter to mediate transcription of foreign DNA sequences and, optionally, an enhancer. Suitable promoters are known in the art and include viral promoters such as those from SV40, cytomegalovirus (CMV), Rous sarcoma virus (RSV), adenovirus (ADV), and bovine papilloma virus (BPV).

The optional presence of an enhancer, combined with the promoter described above, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when placed upstream or downstream from the transcription initiation site, in either normal or flipped orientation, or at a distance of more than 1000 nucleotides from the promoter. See Maniatis, *Science* 236:1237(1987), Alberts, *Molecular Biology of the Cell,* 2nd Ed. (1989). Enhancers derived from viruses may be particularly useful, because they typically have a broader host range. Examples include the SV40 early gene enhancer (see Dijkema, *EMBO J.* 4:761(1985)) and the enhancer/promoters derived from the long terminal repeat (LTR) of the RSV (see Gorman, *Proc. Natl. Acad. Sci.* 79:6777(1982b)) and from human cytomegalovirus (see Boshart, *Cell* 41:521(1985)). Additionally, some enhancers are regulatable and become active only in the presence of an inducer, such as a hormone or metal ion (see Sassone-Corsi and Boreri, *Trends Genet.* 2:215(1986)); Maniatis, *Science* 236:1237(1987)). In addition, the expression vector can and will typically also include a termination sequence and poly(A) addition sequences which are operably linked to the VZV ORFS/L coding sequence.

Sequences that cause amplification of the gene may also be desirably included in the expression vector or in another vector that is co-translated with the expression vector containing an ORFS/L DNA sequence, as are sequences which encode selectable markers. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

The vector that encodes an ORPS/L protein or polypeptide can be used for transformation of a suitable mammalian host cell. Transformation can be by any known method for introducing polynucleotide into a host cell, including, for example packaging the polynucleotide in a virus and transducing a host cell with the virus. The transformation procedure used depends upon the host to be transformed. Methods for introduction of heterologous polynucleotide into mammalian cells are known in the art and include dextran-mediated transfection, calcium phosphate precipitation, polybrene mediated tranfection, protoplast fusion, electroporation, encapsulation of the polynucleotide (s) in liposomes, and direct microinjection of the DNA into nuclei.

Mammalian cell lines available as hosts for expression are known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines.

Insect Cell Expression

The components of an insect cell expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media. Exemplary transfer vectors for introducing foreign genes into insect cells include pAc373 and pVL985. See Luckow and Summers, *Virology* 17:31(1989).

The plasmid can also contains the polyhedron polyadenylation signal and a procaryotic ampicillin-resistance (amp) gene and origin of replication for selection and propagation in *E. coli*. See Miller, *Ann. Rev. Microbiol.* 42:177(1988).

Baculovirus transfer vectors usually contain a baculovirus promoter, i.e., a DNA sequence capable of binding a baculovirus RNA polymerase and initiating the downstream (5' to 3') transcription of a coding sequence (e.g., structural gene) into mRNA. The promoter will have a transcription initiation region which is usually placed proximal to the 5' end of the coding sequence and typically includes an RNA polymerase binding site and a transcription initiation site. A baculovirus transfer vector can also have an enhancer, which, if present, is usually distal to the structural gene. Expression can be either regulated or constitutive.

Yeast And Bacteria Expression

A yeast expression system can typically include one or more of the following: a promoter sequence, fusion partner sequence, leader sequence, transcription termination sequence. A yeast promoter, capable of binding yeast RNA polymerase and initiating the downstream (3') transcription of a coding sequence (e.g. structural gene) into mRNA, will have a transcription initiation region usually placed proximal to the 5' end of the coding sequence. This transcription initiation region typically includes an RNA polymerase binding site (a "TATA Box") and a transcription initiation site. The yeast promoter can also have an upstream activator sequence, usually distal to the structural gene. The activator sequence permits inducible expression of the desired heterologous DNA sequence. Constitutive expression occurs in the absence of an activator sequence. Regulated expression can be either positive or negative, thereby either enhancing or reducing transcription.

Particularly useful yeast promoters include alcohol dehydrogenase (ADH) (EP Patent Pub. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK)(EP Patent Pub. No. 329 203). The yeast PHO5 gene, encoding acid phosphatase, also provides useful promoter sequences. See Myanohara, *Proc. Natl. Acad. Sci. USA* 80:1(1983).

An ORFS/L gene or an active fragment thereof can be expressed intracellularly in yeast. A promoter sequence can be directly linked with an ORFS/L gene or fragment, in which case the first amino acid at the N-terminus of the recombinant protein will always be a methionine, which is encoded by the ATG start codon. If desired, methionine at the N-terminus can be cleaved from the protein by in vitro incubation with cyanogen bromide.

Intraceliularly expressed fusion proteins provide an alternative to direct expression of an ORFS/L sequence. Typically, a DNA sequence encoding the N-terminal portion of a stable protein, a fusion partner, is fused to the 5' end of heterologous DNA encoding the desired polypeptide. Upon expression, this construct will provide a fusion of the two amino acid sequences. For example, the yeast or human superoxide dismutase (SOD) gene, can be linked at the 5' terminus of an ORFS/L sequence and expressed in yeast. The DNA sequence at the junction of the two amino acid sequences may or may not encode a clearable site. See, e.g., EP Patent Pub. No. 196 056. Alternatively, ORFS/L polypeptides can also be secreted from the cell into the growth media by creating a fusion protein comprised of a leader sequence fragment that provides for secretion in yeast or bacteria of the ORFS/L polypeptides. Preferably, there are processing sites encoded between the leader fragment and the ORFS/L sequence that can be cleaved either in vivo or in vitro. The leader sequence fragment typically encodes a signal peptide comprised of hydrophobic amino acids which direct the secretion of the protein from the cell. DNA encoding suitable signal sequences can be derived from genes for secreted yeast proteins, such as the yeast invertase gene (EP Patent Pub. No. 12 873) and the A-factor gene (U.S. Pat. No. 4,588,684). Alternatively, leaders of non-yeast origin, such as an interferon leader, can be used to provide for secretion in yeast (EP Patent Pub. No. 60057). Transcription termination sequences recognized by yeast are regulatory regions located 3' to the translation stop codon. Together with the promoter they flank the desired heterologous coding sequence. These flanking sequences direct the transcription of an mRNA which can be translated into the ORFS/L polypeptide encoded by the ORFS/L DNA.

Typically, the above described components, comprising a promoter, leader (if desired), coding sequence of interest, and transcription termination sequence, are put together in plasmids capable of stable maintenance in a host, such as yeast or bacteria. The plasmid can have two replication systems, so it can be maintained as a shuttle vector, for example, in yeast for expression and in a procaryotic host for cloning and amplification. Examples of such yeast-bacteria shuttle vectors include YEp24 (see Botstein, *Gene* 8:17–24 (1979)), pC1/1 (see Brake, *Proc. Natl. Acad. Sci. USA* 81:4642–4646(1984)), and YRp17 (see Stinchcomb, *J. Mol. Biol.* 158:157(1982)). In addition, the plasmid can be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector may be selected, depending upon the effect on the host of the vector and the ORFS/L polypeptides. See, e.g., Brake, et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. See Orr-Weaver, *Methods In Enzymol.* 101:228–245(1983) and Rine, *Proc. Natl. Acad. Sci. USA* 80:6750(1983).

Typically, extrachromosomal and integrating expression vectors can contain selectable markers to allow for the selection of yeast strains that have been transformed. Selectable markers can include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker can also provide yeast with the ability to grow in the presence of toxic compounds, such as metal. For example, the presence of CUP1 allows yeast to grow in the presence of copper ions. See Butt, *Microbiol. Rev.* 51:351(1987).

Alternatively, some of the above described components can be put together into transformation vectors. Transformation vectors are typically comprised of a selectable marker that is either maintained in a replicon or developed into an integrating vector, as described above. Expression and transformation vectors, either extrachromosomal or integrating, have been developed for transformation into many yeasts. Exemplary yeasts cell lines are *Candida albicans* (Kurtz, *Mol. Cell. Biol.* 6:142(1986), *Candida maltosa* (Kunze, *J. Basic Microbiol.* 25:141(1985), *Hansenula polymorpha* (Gleeson, *J. Gen. Microbiol.* 132:3459(1986) and Roggenkamp, *Mol. Gen. Genet.* 202:302(1986), *Kluyveromyces fragilis* (Das, *J. Bacteriol.* 158:1165(1984), *Kluyveromyces lactis* (De Louvencourt, *J. Bacteriol.* 154:737(1983) and Van den Berg, *Bio/Technology* 8:135(1990), *Pichia guillerimondii* (Kunze, *J. Basic Microbiol.* 25:141(1985), *Pichia pastoris* (Cregg, *Mol. Cell. Biol.* 5:3376 (1985), *Saccharomyces cerevisiae* (Hinnen, *Proc. Natl. Acad. Sci. USA* 75:1929(1978) and Ito, *J. Bacteriol.* 153:163(1983), *Schizosaccharomyces pombe* (Beach and Nurse, *Nature* 300:706(1981), and *Yarrowia lipolytica* (Davidow, *Curr. Genet.* 10:380471(1985) and Gaillardin, *Curr. Genet.* 10:49 (1985).

Methods of introducing exogenous DNA into yeast hosts are well-known in the art, and typically include either the transformation of spheroplasts or of intact yeast cells treated with alkali cations. Transformation procedures usually vary with the yeast species to be transformed. See the publications listed in the foregoing paragraph for appropriate transformation techniques.

Additionally, the ORFS/L gene or fragment thereof can be expressed in a bacterial system. In such system, a bacterial promoter is any DNA sequence capable of binding bacterial RNA polymerase and initiating the downstream (3') transcription of a coding sequence (e.g. a desired heterologous gene) into mRNA. A promoter will have a transcription initiation region which is usually placed proximal to the 5' end of the coding sequence. This transcription initiation region typically includes an RNA polymerase binding site and a transcription initiation site. A bacterial promoter can also have a second domain called an operator, that can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*). See Raibaud, *Ann. Rev. Genet.* 18:173(1984). Regulated expression can therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (Lac) (see Chang, *Nature* 198:1056(1977), and maltose. Additional examples include promoter sequences derived from biosynthetic enzymes such as tryptophan (trp) (see Goeddel, *NUC. ACIDS RES.* 8:4057(1981), Yelverton, *Nuc. Acids Res.* 9:731(1981), U.S. Pat. No. 4,738,921 and EP Patent Pub. Nos. 36 776 and 121 775). The lactomase (bla) promoter system (see Weissmann, *Interferon* 3 (ed. I. Gresser), the bacteriophage lambda PL promoter system (see Shimatake, *Nature* 292:128(128) and the T5 promoter system (U.S. Pat. No. 4,689,406) also provides useful promoter sequences.

In addition, synthetic promoters which do not occur in nature also function as bacterial promoters. For example, transcription activation sequences of one bacterial or bacteriophage promoter can be joined with the operon sequences of another bacterial or bacteriophage promoter, creating a synthetic hybrid promoter such as the tac promoter (see U.S. Pat. No. 4,551,433, Amann, *Gene* 25:167 (1983) and de Boer, *Proc. Natl. Acad. Sci.* 80:21(1983)). A bacterial promoter can include naturally occurring promoters of non-bacterial origin that have the ability to bind bacterial RNA polymerase and initiate transcription. A naturally occurring promoter of non-bacterial origin can be coupled with a compatible RNA polymerase to produce high levels of expression of some genes in prokaryotes. The bacteriophage T7 RNA polymerase/promoter system is exemplary. (see Studier, *J. Mol. Biol.* 189:113(1986) and Tabor, *Proc. Natl. Acad. Sci.* 82:1074(1985)).

In addition to a functioning promoter sequence, an efficient ribosome binding site is also useful for the expression of the ORFS/L gene or fragment thereof in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon (see Shine, *Nature* 254:34(1975). The SD sequence is thought to promote binding of mRNA to the ribosome by the pairing of bases between the SD sequence and the 3' and of *E. coli* 16S rRNA (see Steitz, *Biological Regulation and Development: Gene Expression* (ed. R. F. Goldberger)(1979)).

ORFS/L protein can be expressed intracellularly. A promoter sequence can be directly linked with an ORFS/L gene or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase. See EP Patent Pub. No. 219 237.

Fusion proteins provide an alternative to direct expression. Typically, a DNA sequence encoding the N-terminal portion of an endogenous bacterial protein, or other stable protein, is fused to the 5' end of heterologous ORFS/L gene coding sequences. Upon expression, this construct will provide a fusion of the two amino acid sequences. For example, the bacteriophage lambda cell gene can be linked at the 5' terminus of an ORFS/L gene or fragment thereof and expressed in bacteria. The resulting fusion protein preferably retains a site for a processing enzyme (factor Xa) to cleave the bacteriophage protein from the ORFS/L gene or fragment thereof (see Nagai, *Nature* 309:810(1984). Fusion proteins can also be made with sequences from the lacZ gene (Jia, *Gene* 60:197(1987),the trpE gene (Allen, *J. Biotechnol.* 5:93(1987) and Makoff, *J. Gen. Microbiol.* 135:11(1989), and the Chey gene (EP Patent Pub. No. 324 647) genes. The DNA sequence at the junction of the two amino acid sequences may or may not encode a clearable site. Another example is a ubiquitin fusion protein. Such a fusion protein is made with the ubiquitin region that preferably retains a site for a processing enzyme (e.g., ubiquitin specific processing-protease) to cleave the ubiquitin from the ORFS/L polypeptide. Through this method, mature ORFS/L polypeptides can be isolated. See Miller, *Bio/Technology* 7:698(1989).

Alternatively, ORFS/L proteins or polypeptides can also be secreted from the cell by creating chimeric DNA molecules that encode a fusion protein comprised of a signal peptide sequence fragment that provides for secretion of the ORFS/L proteins or polypeptides in bacteria. (See, for example, U.S. Pat. No. 4,336,336). The signal sequence fragment typically encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the ORFS/L protein or polypeptide.

DNA encoding suitable signal sequences can be derived from genes for secreted bacterial proteins, such as the *E. coli* outer membrane protein gene (ompA) (Masui, Experimental Manipulation of Gene Expression (1983) and Ghrayeb, *EMBO J.* 3:2437(1984)) and the *E. coli* allie phosphatase signal sequence (phoA) (see Oka, *Proc. Natl. Acad. Sci.* 82:7212(1985). The signal sequence of the alpha-amylase gene from various Bacilus strains can be used to secrete heterologous proteins from *B. subtilis* (see Palva, *Proc. Natl. Acad. Sci.* 79:5582(1982) and EP Patent Pub. No. 244 042).

Transcription termination sequences recognized by bacteria are regulatory regions located 3' to the translation stop codon. Together with the promoter they flank the coding sequence. These sequences direct the transcription of an mRNA which can be translated into the ORFS/L protein or polypeptide encoded by the ORFS/L DNA sequence. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the promoter, signal sequence (if desired), coding sequence of interest, and transcription termination sequence are maintained in an extrachromosomal element (e.g., a plasmid) capable of stable maintenance in the bacterial host. The plasmid will have a replication system, thus allowing it to be maintained in the bacterial host either for expression or for cloning and amplification. In addition, the plasmid can be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. See e.g., EP Patent Pub. No. 127 328.

Typically, extrachromosomal and integrating expression constructs can contain selectable markers to allow for the selection of bacterial strains that have been transformed. Selectable markers can be expressed in the bacterial host and can include genes which render bacteria resistant to drugs such as ampicillin, chloramphenicol, erythromycin, kanamycin (neomycin), and tetracycline (see Davies, *Ann. Rev. Microbiol.* 32:469(1978). Selectable markers can also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in an extrachromosal vector or an integrating vector, as described above.

Expression and transformation vectors, either extrachromosomal or integrating, have been developed for transformation into many bacteria. Exemplary are the expression vectors disclosed in Palva, *Proc. Natl. Acad. Sci.* 79:5582 (1982), EP Patent Pub. Nos. 036 259 and 063 953 and PCT Patent Publication WO 84/04541 (for *B. subtilis*); in Shimatake, *Nature* 292:128(1981), Amann, *Gene* 40:183 (1985), Studier, *J. Mol. Biol.* 189:113(1986) and EP Patent Pub. Nos. 036 776, 136 829 and 136 907 (for *E. coli*); in Powell, *Appl. Environ. Microbiol.* 54:655(1988) and U.S. Pat. No. 4,745,056 (for Streptococcus).

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Exemplary methodologies can be found in Masson, *FEMS Microbiol. Let.* 60:273(1989), Palva, *Proc. Natl. Acad. Sci.* 79:5582(1982), EP Patent Pub. Nos. 036 259 and 063 953 and PCT Patent Pub. WO 84/04541 for Bacillus transformation. For campylobacter transformation, see e.g., Miller, *Proc. Natl. Acad. Sci.* 85:856(1988) and Wang, *J. Bacteriol.* 172:949(1990). For *E. coli*, see e.g., Cohen, *Proc. Natl. Acad. Sci.* 69:2110(1973), Dower, *Nuc. Acids Res.* 16:6127 (1988), Kushner, *Genetic Engineering: Proceedings of the International Symposium on Genetic Engineering* (eds. H. W. Boyer and S. Nicosia), Mandel, *J. Mol. Biol.* 53:159 (1970) and Taketo, *Biochem. Biophys. Acta* 949:318(1988). For Lactobacillus and Pseudomonas, see e.g., Chassy, *FEMS Microbiol. Let.* 44:173(1987) and Fiedler, *Anal. Biochem.* 170:38(1988), respectively. For Streptococcus, see e.g., Augustin, *FEMS Microbiol. Let.* 66:203(1990), Barany, *J. Bacteriol.* 144:698(1980), Harlander, *Streptococcal Genetics* (ed. J. Ferretti and R. Curtiss III)(1987), Perry, *Infec. Immun.* 32:1295(1981), Powell, *Appl. Environ. Microbiol.* 54:655(1988) and Somkuti, *Proc. 4th Evr. Cong. Biotechnology* 1:412(1987).

The present invention is illustrated by the following examples.

EXAMPLE 1

Identification of ORFS/L Gene in the Dumas Strain

The full DNA sequence of the Dumas strain of VZV is known. The linear DNA sequence of VZV (GenBank Accession Number X04370) was searched for sequences similar to the herpes simplex virus $\gamma_1$ 34.5 gene. Computer assisted sequence analysis of VZV open reading frames (ORFs) yielded no significant homology to the $\gamma_1$34.5 gene.

The Dumas VZV genomic nucleotide sequence was further analyzed with the assistance of a computer. It was observed that out of the nine possible reading frame orientations, a first ORF in the $TR_L$ and $U_L$ sequence and a second ORF in the $IR_S$ and $IR_L$ sequence or a first ORF in the $TR_L$ and $U_L$ sequence and a third ORF in the $TR_S$ sequence could be joined to produce a single reading frame of 224 amino acids. As shown in FIG. 2, these ORFs correspond to the joining of the striped region representing the first ORF in FIG. 2 with either of the 3' solid regions representing the second and third ORFs of the $U_L$-Par isomer shown. In the VZV lifecycle the ORFS/L gene is formed by different VZV genomic structures, the $U_L$-Inv isomer, $U_L$-Par concatamer junctions or $U_L$-Par circles as shown in FIG. 2.

The ORFS/L (Dumas) gene shows no significant sequence homology to any gene using the standard PAM 120 alignment matrices for database searching. Using the BLOSUM62 alignment matrix, however, the herpes simplex $\gamma_1$ 34.5 gene and the ORFS/L (Dumas) gene scored a weak homology. (The databases searched were the Gen Bank, Swis-Prot, PDB, and PIR databases.) Because the proline content of both genes is high this homology may be biased.

The full DNA sequence of the ORFS/L (Dumas) gene comprising the first ORFS/L reading frame joined to the second ORFS/L reading frame is shown in FIG. 5 along with its encoded amino acid sequence. The nucleic acid sequence of the ORFS/L (Dumas) gene comprised of the first ORFS/L reading frame joined to the third ORFS/L reading frame is identical to the ORFS/L (Dumas) gene made of the first and second reading frames.

The first ORF corresponds to the VZV (Dumas) genomic nucleotide sequences 1 through 562, including a stop codon ending at position 562. This nucleotide sequence encodes the C-terminal 168 amino acids of the ORFS/L protein. The second ORF corresponds to the VZV (Dumas) genomic nucleotides 104,925 through 105,125 and the third ORF corresponds to the VZV (Dumas) genomic nucleotides 124,772 through 124,884. Either the second or third ORFs can encode the N-terminal 66 amino acids of the ORFS/L protein. The ORFS/L (Dumas) gene nucleotide sequence and corresponding 224 amino acid sequence is shown in FIG. 5 (SEQ ID NO:9 and 10, respectively). A comparison of the Dumas ORFS/L gene nucleotide sequence with the PCR and genomic ORFS/L gene nucleotide sequences, discussed herein, is shown in FIG. 7.

ORFS/L gene has been refractory to discovery and is not listed as VZV open reading frame with a translatable product in any of the known data banks, e.g., in GenBank. The standard linear display format used to represent VZV sequences prevents the detection of a complete open reading frame. ORFS/L (Dumas) also lacks an adjacent canonical promoter TATA element and poly A addition signal AATAAA that are commonly used as gene identification criteria.

Although amino acid alignment revealed little or no homology between ORFS/L and $\gamma_1$34.5, the position of ORFS/L gene in the VZV genome shows similarity to the position of $\gamma_1$34.5 in the HSV genome. The $\gamma_1$34.5 gene is located within the 8 kbp internal and terminal long repeat sequences in the herpes simplex virus genome. Its N-terminus is located in close proximity to the junction of the long and short regions and the gene is positioned immediately upstream of the potent transactivator gene, ICP0. In similar manner, the N-terminal region of ORFS/L is located near the long and short junction in VZV. By using the long-short junction as a point of reference, ORFS/L lies just upstream (but on the opposite end of the $U_L$ segment) of the positional homolog to the herpes simplex virus ICP0 gene.

EXAMPLE 2

Identification and Isolation of ORFS/L (Oka) Gene in the Oka Strain

The existence of the ORFS/L gene in the Oka strain of VZV was confirmed and the DNA encoding the ORFS/L gene was isolated using a polymerase chain reaction (PCR)-based strategy using oligonucleotide primers designed from the sequence of VZV (Dumas) to amplify the DNA fragment containing a complete ORFS/L (Oka) gene as shown in FIG. 3. Convenient restriction enzyme sites were included at the 5' ends of the primers. Because linear molecules of VZV DNA (which comprise ~95% of the packaged molecules in VZV nucleocapsids) do not contain an intact ORFS/L sequence they were not usable for the PCR cloning. Only genomes in which the $U_L$ sequence has inverted (~5% of packaged genomes) contain an intact ORFS/L gene and are usable as shown in FIG. 3. Similarly, circular or concatameric DNA also contain an intact version of the ORFS/L gene and were amplifiable using PCR. These latter forms can be found during the replication cycle of VZV.

PCR primers were generated based upon the sequence of VZV (Dumas). Primer 3 had the following sequence:

5'-gccgccaTGGAGGGGAGCGACGGAACACG-3' SEQ ID NO:1

The nucleotides in upper case correspond to nucleotides 124,326 to 124,327 and the complementary strand of nucleotides 105,550 to 105,571 of the VZV (Dumas) DNA sequence.

Primer 4 had the following sequence:

5'-gccgccatGGCTGTCGGCGGACTATGAAC-3' SEQ ID NO:2

The nucleotides in upper case correspond to the complementary strand of nucleotides 1906 to 1926 of the VZV (Dumas) DNA sequence. In both primers, the lower case nucleotides add an NcoI site to the PCR product and do not correspond to VZV DNA sequence.

Primer 3 was designed to hybridize to viral DNA approximately 450 nucleotides upstream from the predicted ORFS/L start codon and Primer 4 was designed to hybridize to viral DNA approximately 60 bp downstream of the stop codon in the ORF2, leading to a predicted PCR product approximately 2.5 kb in length as shown in FIG. 3.

PCR was performed using Primers 3 and 4 on viral DNA isolated from either the cytoplasm or nucleus of a VZV (Oka) infected human foreskin fibroblast culture using standard techniques. See, PCT application WO 93/24616. A band having the predicted length was seen on an agarose gel after the PCR reaction. The PCR reactions were treated with NcoI, fractionated on an agarose gel, and the proper sized DNA fragment was isolated and ligated into the NcoI digested plasmid pGEM5Zf+. One clone from PCR material generated from the cytoplasmic DNA fraction was isolated and designated pS/L C3.

EXAMPLE 3

Sequencing of the ORFS/L (Oka) Gene from a PCR Fragment

The Sacd to BamHI fragment comprising the ORFS/L gene in the plasmid pS/L C3 of Example 2 above was isolated and inserted into the M13 cloning vector, M13mp18. Specifically, a plaque containing the appropriate insert was isolated and designated M13S/LC3.

Primers were designed to hybridize to the S/L region of the M13 clone and used to sequence the DNA of ORFS/L gene using the dideoxy chain termination method of DNA sequencing. The resulting nucleotide sequence and amino acid sequence is set forth in FIG. 6*a*.

EXAMPLE 4

Comparison of Oka ORFS/L Gene Sequence and the Dumas ORFS/L Gene Sequence

The M13S/L C3 Oka ORFS/L gene sequence is 1121 nucleotides in length and corresponds to the nucleotide sequence shown in FIG. 6*a* (SEQ ID NO:11). The M13S/L C3 Oka ORFS/L protein sequence is 223 amino acids in length and is shown in FIG. 6*a* (SEQ ID NO:12).

The entire ORF for M13S/L C3 aligns with the ORFS/L (Dumas) protein sequence with a matching percentage of 84%.

In accordance with known techniques, all or a fragment of the nucleotide sequence embodying ORFS/L protein can be placed in an expression vector system to produce all or a fragment of the ORFS/L protein or polypeptide, as discussed previously. The ORFS/L protein can be purified using standard techniques. The immunogenicity of the protein can be assessed using such techniques as are also known in the art. For example, guinea pigs can be inoculated intramuscularly with an admixture of the purified, recombinantly produced, ORFS/L protein or fragment thereof and complete Freund's adjuvant, followed by booster inoculations one month later as is disclosed in U.S. Pat. No. 4,686,101 (herein incorporated by reference in its entirety). Sera is then obtained from the guinea pigs and tested in an in vitro VZV neutralization assay as described in Keller, J., *Virology,* 52:293 (1984) to determine whether it elicits VZV neutralizing antibodies in comparison to pre-immunization sera.

EXAMPLE 5

Sequencing of the ORFS/L (Oka) Gene from VZV Genomic DNA

The ORFS/L gene of Oka was also sequenced using genomic VZV DNA. As discussed herein VZV (Oka) DNA was cut into four overlapping fragments and placed into cosmids for amplication of VZV DNA for various purposes. Three plasmid, pV4L, pV21J and pV21S, were made from the cosmids described herein, and contain the first, second and third ORFs from the ORFS/L gene. The plasmid names refer to the lefthand most region of the VZV genome (pV4L), the junction between $IR_L$ and $IR_S$ sequences in the VZV genome (pV21J), and the righthand most region of the VZV genome (pV21S).

To produce pV4L the cosmid pVFsp4, described herein, was digested with BamHI to liberate a 920 base pair Oka DNA fragment (corresponding to the nucleotides 1 to 920 of the Dumas sequence). The 920 base pair fragment was isolated and inserted into BamHI digested pGEM7zf+ using standard techniques. Restriction digests yielded the expected restriction fragmentation patterns.

To produce pV21S, the cosmid pVSpe21, described herein, was digested with BamHI, to liberate a 1921 base pair Oka DNA fragment (corresponding to nucleotides 122,963 through 124,884 of the Dumas sequence). The 1921 base pair fragment was isolated and inserted into BamHI digested pGEM7zf+ using standard. Restriction digests of plasmid pV21S yielded the expected restriction fragmentation patterns.

To produce pV21J, the cosmid pVSpe21, described herein, was digested with BamHI and Bgln to liberate a 2861 base pair Oka DNA fragment (corresponding to nucleotides 106,931 through 104,170 of the Dumas nucleotide sequence). The 2861 base pair fragment was isolated and inserted into a BamHI digested pGEM7zf+. Restriction digest of the plasmid pV21J yielded the expected restriction fragmentation patterns.

These three plasmids, pV4L, pV21J, and pV21S encoding the first, second and third ORFs, respectively, were sequenced using double stranded sequencing techniques, as is well known in the art.

The nucleotide and amino acid sequences for the first ORF of the ORFS/L gene of Oka are shown in FIG. 6b (SEQ ID NO:13 and 14, respectively). The nucleotide sequences of the second and third ORFs are nearly identical as shown in FIG. 7 (SEQ ID NO:15 and 16, respectively).

With respect to the PCR clone, p S/L C3, the nucleotide sequence of the first, second and third ORFs of Oka correspond to the respective nucleotide sequences from p S/L C3, with the exception that there is a extra G in the first ORF of the Oka genomic DNA strain. The extra G in the Oka strain is located in the corresponding location the Dumas sequence between nucleotides 124,884 and 1 of the Dumas genomic sequence (the extra "G" arises from the unpaired 3' extension of the VZV genome). The extra G shifts the reading frame in Oka to make the start ATG correspond to nucleotide 88 of the Dumas genomic sequence. Instead of encoding a protein identical to the 223 amino acid ORFS/L protein of the p S/L C3 DNA, the ORFS/L gene of Oka produces an 157 amino acid protein with a-molecular weight of 17,123 daltons. The extra "G" is also shown and compared to the sequences described herein in FIG. 7.

EXAMPLE 6

Construction of Cosmid Clones of the VZV (Oka) Genome

Because VZV is difficult to grow in cell culture (see for example PCT patent publication WO 93/24616 published Dec. 9, 1993), an alternative method making reconstructed VZV was developed. Briefly, four overlapping fragments spanning the entire VZV (Oka) genome were constructed, amplified and transfected into eukaryotic cells using four cosmids. The four cosmids are referenced as pV Fsp4, pV Spe5, pV Pme19, and pV Spe21 and shown in FIG. 4. The overlapping VZV fragments in these cosmids recombine in the transfected cell, producing an intact reconstructed viral genome and an infectious reconstructed VZV. At least one of the four cosmids can contain the desired mutation to the ORFS/L gene, as well as, the viral genomic DNA. The general procedures set forth here could be used for any strain of VZV or could be used to make chimeric viruses and chimeric genomes with other viruses, such as herpes simplex virus A. VZV DNA Isolation To make these VZV cosmid clones, DNA was isolated from the nucleocapsids of VZV (Oka) by the method of Straus (J. Virol 40:516–525, 1981), as follows. Twelve 850 $cm^2$ roller bottles of confluent human foreskin fibroblast (HF) cells were infected with a frozen stock of previously, VZV (Oka) infected HF. Three days post infection (at a time when nearly all the cells were rounded and showed cytopathic effect (CPE)) the nucleopcapsids were harvested.

The cells were shaken off the roller bottles into the media. The media was collected and centrifuged at approximately 200×g to pellet the cells. The cells were disrupted by freezing and thawing three times alternately in a dry ice-acetone bath and 37° C. water bath. The cells were resuspended in lysis buffer (30 mM Tris, pH 7.5; 0.5% NP-40; 0.5% deoxycholate; 3.6 mM $CaCl_2$; 5 mM Mg acetate; 125 mM KC1) containing 25 μg/ml DNAseI and 25 μg/ml RNAseA. Following digestion for 30 minutes, at 30° C., the lysate was extracted one time with 1/2 volume of trichlorotrifluoroethane. The supernatant was placed on top of a step gradient of 5% glycerol/40% glycerol in lysis buffer lacking $CaCl_2$ and magnesium acetate. The material was centrifuged for 60 min. at 100,000×g at 4° C. The resulting pellet contained the viral nucleocapsids from which VZV DNA was then isolated.

The nucleocapsid pellet was resuspended in 50 mM Tris, pH 7.5, 10 mM EDTA. SDS was added to a final concentration of 1% and proteinase K was added to a final concentration of 200 μg/ml. The nucleocapsids were digested for 60 min at 65° C. The DNA was obtained by extracting the digest three times with equal volumes of water saturated, buffered phenol and chloroform (24 parts chloroform:1 part isoamyl alcohol). The DNA was then dialyzed overnight against 10 mM Tris, pH 7.5/2 mM EDTA.

This DNA was the source of the DNA used for generating the cosmid clones used in regenerating infectious mutant VZV virus as set forth herein.

B. Construction of Adaptors

In order to easily insert and excise VZV DNA into and from the constructed cosmids, adaptors, short double-stranded oligonucleotides with different termini, were synthesized on an Applied Biosystems (Foster City, Calif.) instrument according to manufacturer instructions. These adaptors were ligated to restriction digested VZV(Oka) DNA to yield restriction fragments compatible with the cosmid vector described below. Three characteristics were incorporated into the design of the adaptors: 1. One end is blunt. This terminus was used to ligate to the restricted VZV DNA. 2. The opposing end of the adaptor was compatible with Bamli restricted DNA because the cosmid vector was to be digested with BamHI. 3. The internal nucleotides constituted an Asc1 restriction enzyme site. Digestion of cosmids containing the restriction fragmented VZV DNA ligated by these flanking adaptors separated the VZV DNA from the cosmid vector (because there are no AscI sites in the VZV(Oka) genome). The adapters used were:

| | |
|---|---|
| Oligonucleotide: "Bam-Asc Adaptor" | "Blunt Asc" |
| 5'-GATCCGGCGCGCCA-3' | 5'-TGGCGCGCCG-3' |
| SEQ ID NO: 3 | SEQ ID NO: 4 |

Approximately 5,000 pmols of "Blunt Asc" was phosphorylated at the 5' end by incubation with ATP and T4 polynucleotide kinase.

Approximately 5,000 pmols of "Blunt Asc" and "Bam-Asc Adaptor" were electrophoresed onto a 20% polyacrylamide/7M urea gel. Following electrophoresis, the predominant bands were visualized by UV shadowing and excised from the surrounding gel. The oligonucleotides were eluted from the gel and purified on a Sep-pak C18 column according to the manufacturer's instructions. The quantity of each oligonucleotide was assessed by spectrophotometry.

500 pmols each of "Bam-Asc Adaptor" and "Blunt Asc" were mixed together. The mixture was diluted to a final concentration of 20 pmol/μl of each oligonucleotide; 50 mM NaCl; 10 mM Tris; 10 mM MgCl$_2$; 1 mM DTT, pH 7.9 @ 25° C. The mixture was heated to 95° C. for 3 minutes and slowly cooled to room temperature (approximately 25 ° C.). This procedure produced a double stranded oligo with the following characteristics:

| | |
|---|---|
| 5'-PO$_4$-TGGCGCGCCG-3' | SEQ ID NO:4 |
| 3'-ACCGCGCGGCCTAG-OH-5' | SEQ ID NO:3 |

C. Ligation of Adaptors to VSV (Oka) DNA

The VZV DNA prepared as described in part A above was subjected to restriction digestion in order to generate four fragments for ligation into four cosmids using the adapters. Based on the VZV genomic sequence of the Dumas strain, the following four restriction fragments were predicted to result from individual restriction digests using Fsp1, Spe1 and Pme1 restriction enzymes.

Fsp1: nucleotides (L terminus) 1 to 33211

Spe1: nucleotides: 21875 to 62008

Pme1: nucleotides: 53877 to 96188

Spe1: nucleotides: 94208 to 124,884 (S terminus)

Restriction digests of VZV (Oka) DNA are consistent with these predicted sizes.

To generate these restriction fragments, approximately 2.5 μg of the VZV (Oka) nucleocapsid DNA form Part A above was separately digested with either Fsp1, Spe1, or Pme1, as recommended by the manufacturer. The Spe1 and Fsp1 digests were subsequently made blunt ended by incubation with dNTPs and T4 DNA polymerase. Pme1 releases the fragment as blunt ended and requires no such treatment.

100 pmols of the adaptors prepared in Part B above were then ligated to the blunt ended VZV DNA. See Maniatis, T. et al, *Molecular Cloning* (1991). Following ligation, excess adaptors that had not ligated to the VZV DNA were removed by chromatography on a 2 ml Sepharose CL-4B column equilibrated in 10 mM Tris, pH 7.5; 2 mM EDTA; 100 mM NaCl.

SuperCos™ 1 is a cosmid vector available from Stratagene (La Jolla, Calif.). The vector was prepared according to the manufacturer's instructions. In brief, the vector was digested with Xba1 and dephosphorylated. The vector was next digested with BamHI to yield two DNA fragments, both of which are ligated to the VZV fragment DNA to form a cosmid containing a 15–35 kb fragment of VZV genomic DNA.

To perform the ligation, approximately 3 μg of the SuperCos™ 1 vector (containing both BamnHI fragments) was ligated to VZV DNA with Asc I adaptors using ligase. Following ligation, the mixture was packaged into lambda phage particles using a commercially available packaging extract (Gigapack II packaging extract, Stratagene, La Jolla, Calif.). The packaged DNA was introduced into the *E. coli* strain XL1-MR (Stratagene, La Jolla, Calif.). Transfected bacteria were plated onto LB-ampicillin plates for selection and grown overnight at 37° C.

Individual ampicillin resistant colonies were picked and grown to late log phase in LB-ampicillin broth. The cosmid DNA was isolated from the bacteria using techniques known in the art, digested with BamHI and electrophoresed on an agarose gel. Each cosmid yielded a distinct and predictable pattern. Two cosmid clones containing each restriction fragment were identified and isolated. Their designations are as follows:

Fsp1 (1-33211): pV Fsp 4 and pV Fsp 25

Spe1 (21875-62008): pV Spe 5 and pV Spe I4

Pme1 (53877-96188): pV Pme I9 and pV Pme 26

Spe1 (94208-124884): pV Spe 21 and pV Se 24

Large cultures of these cosmids were grown and the DNA isolated by methods known in the art.

EXAMPLE 7

ORFS/L Gene Mutations and Cosmids

Cosmid clones containing mutant VZV ORFS/L genes were constructed using a cosmid clone containing a wildtype VZV ORFS/L gene and a plasmid clone containing the PCR product of the entire ORSF/L gene as follows.

The first mutant VZV ORFS/L gene constructed was a deletion of nearly the entire first reading frame of the ORFS/L gene ("first ORF") (amino acids 99 through 223 of FIG. 6*a* were deleted), equal to approximately 60% of the ORFS/L gene. The deletion mutant was constructed using the pV Fsp4 cosmid which contains the VZV (Oka) nucleotide sequence (corresponding to VZV (Dumas) genomic nucleotides 1 through 33211) and contains the first ORF of the ORFS/L gene. Accordingly, pV Fsp4 was digested with XhoI and PmeI to isolate a predicted 1190 nucleotide VZV (Oka) fragment (corresponding to VZV (Dumas) genomic nucleotides 24 through 1214) which was then ligated into a pGEM7zf+ plasmid previously digested with XhoI and SacI. The 3' overhang of the SacI site was made blunt ended by the addition of T4 DNA polymerase in order to facilitate ligation. The resulting clone, containing the first ORF of the VZV (Oka) ORFS/L gene, was designated pV XLeft4 (containing nucleotides corresponding to Dumas nucleotide sequence 24 through 1214).

In order to delete nearly all of the first ORF (the last 60% of the VZV (Oka) first ORF), pV XLeft4 was then partially digested with the enzyme ApaLI. (Partial digestion was necessary to excise one fragment because ApaLI cuts once within the VZV insert of pV XLeft4 (nucleotide 183 of VZV(Dumas)) and twice within the pGEM7zf+ vector.) Following partial digestion with ApaLI, the digested DNA was phenol/chloroform extracted to remove enzyme, the correct size fragment (containing both vector and the first ORF) isolated and then digested to completion with BspEI. BspEI cuts at nucleotide 571 of the corresponding VZV (Dumas) nucleotide sequence. The BspEI site is less than 10 nucleotides downstream of the ORFS/L gene termination codon in the first ORF. Thus, BspEI digestion releases an approximately 388 bp fragment from the first ORF. Following digestion with BspEI, the two ends (ApaLI and BspEI) of the ApaL1/BspEI fragment (also containing the vector) were made blunt by the addition of Klenow enzyme and the appropriate deoxynucleotides. The blunt ended DNA was separated on an agarose gel, the appropriately sized fragment eluted, ligated with itself and used to transform *E. coli* using methods known in the art. The resulting plasmid encompasses a deletion of the nucleotides between the ApaLI site within the ORF S/L gene and the BspEI site downstream of ORF S/L. This plasmid was designated pV Left delta4 and encodes VZV Oka nucleotides 225 through 383 where 383 is linked to 772 through 1214 (nucleotide 1121 is the last sequenced nucleotide) (which correspond to the Dumas sequence nucleotides 24 through 183, and 572 through 1214 where 183 is linked to 572).

The second mutant VZV ORFS/L gene constructed contained an insertion of the gB epitope encoding nucleotide sequence of Cytomegalovirus (CMV) at the C-terminus of the first ORF. This mutant was constructed using the plasmid pG S/L C3 which contains the cloned, sequenced PCR product of the entire intact the VZV Oka ORFS/L nucleotide sequence (1121 nucleotides in length). Accordingly, pG S/L C3 was digested with EcoRI and XbaI to remove the nucleotide sequence encoding the last 37 C-terminal amino acids of the ORFS/L gene and to create a site for inserting a double stranded oligonucleotide encoding the gB epitope. (EcoRI cuts at nucleotide 444 of the corresponding VZV (Dumas) sequence and XbaI cuts in the polylinker of the plasmid downstream from the ORFS/L termination codon.) The resulting EcoRI/XbaI site provided an insertion site for a double stranded oligonucleotide with EcoRI and XbaI sticky ends, codons for the 20 amino acid CMV gB epitope, a stop codon at the end of the epitope, and a KpnI site downstream of the termination codon. Two single stranded oligonucleotides, "S/L R1RevgB" and "S/L R1CodegB", with the following sequences:

CTAGGGTACC TTAGTGGCGA TATCCGTTCT TGCGGTG-
GCG GAGGCGGTCG AGGAGGTTGG GCTTCTGCCC CTT
(S/L R1RevB) (SEQ ID NO:5), and AATTAAGGGG CAGAAGCCCA ACCTCCTCGA CCGCCTC-
CGC CACCGCAAGA ACGGATATCG CCACTAAGGT ACC
(S/L R1CodegB) (SEQ ID NO:6)

were annealed to make the double stranded oligonucleotide. The double stranded oligonucleotide was ligated into the EcoRI/XbaI site and the resulting plasmid, pG ORFS/L CgB-7, was isolated using standard techniques. The region of pG ORFS/L CgB-7 within and surrounding the oligonucleotide insertion was sequenced and confirmed to have the predicted sequence. This plasmid, pG ORFS/L CgB-7, contains an ORFS/L gene in which the nucleotides encoding the C-terminal 37 amino acids of ORF S/L are replaced by the nucleotides encoding the 20 amino acids of the CMV gB epitope (herein referred to as "ORFS/L-CgB insert").

The first ORF with its C-terminal 37 amino acids replaced with the gB eptiope (herein referred to as "first ORF-CgB") was removed from the ORFS/L-CgB insert of pG ORFS/L CgB-7 and subcloned into a pGEM7zf+ vector for final insertion into a pV Fsp4 cosmid as follows. The first ORF-gB sequence of pG ORFS/L CgB-7 was excised by digestion with Kpn I and XhoI (corresponding to nucleotide 24 to 444 of the Dumas nucleotide sequence, plus the 20 amino acid CMV gB epitope and the KpnI site). The KpnI site in the excised fragment was converted to a blunt ended site by the addition of T4 DNA polymerase and the appropriate nucleotides. The blunt end KpnI/XhoI fragment was inserted into pV XLeft4 plasmid (the pGEM7zf+ vector containing the first ORF used for the deletion mutant) previously digested with BspEI (made blunt ended by the addition of Klenow and the appropriate deoxynucleotides) and XhoI. This step replaced the deletion mutant insert, discussed above, with the first ORF-CgB sequence. The resulting plasmid with the first ORF-CgB sequence and about 700 base pairs of VZV Oka DNA was designated pV XLeft4gB (corresponding to Dumas sequence nucleotides 24–444 lied to the nucleotide sequence encoding the CMVgB epitope and a blunt ended KpnI site appended to nucleotides corresponding to Dumas sequence nucleotides 572–1214, where the blunt ended KpnI site is linked to nucleotide 572).

The inserts from pV XLeft delta4 and pV XLeft4gB, first ORF deletion mutant and first ORF-CgB mutant (respectively), were cloned into VZV genomic DNA contained within two separate pV Fsp4 cosmids as follows. The cosmid pV Fsp4 was digested to completion with XhoI (cuts at nucleotide 24 in the corresponding Dumas nucleotide sequence) and SgrA1 (cuts at nucleotide 28743 in the corresponding Dumas nucleotide sequence) to release a 12 kilobase pair vector fragment containing the vector and about 5 kilobase pairs of VZV Oka DNA (corresponding to nucleotides 28,743 through 33,211 of the VZV Dumas nucleotide sequence). Fragments isolated using restriction enzymes XhoI (which cuts at nucleotide 24 in the corresponding Dumas nucleotide sequence) and SgrAI (which cuts at nucleotide 777 in the corresponding Dumas nucleotide sequence) from plasmids pV XLeft delta4 and pV XLeft4gB were inserted into the corresponding sites of the 12 kbp vector fragment. The resulting cosmids were designated pV dSgr d4 (containing the Oka nucleotide sequences corresponding to the Dumas nucleotide sequence 24 through 183 linked to 572 through 1214, where nucleotide 183 is linked to nucleotide 572) and pV dsgr 4gB (containing Oka nucleotide sequences corresponding to the Dumas nucleotide sequences 24 through 444 appended to nucleotides encoding CMV gB epitope and blunt ended KpnI site, where the last nucleotide in the blunt ended KpnI site is linked to 572 through 1214).

In order to replace the removed VZV DNA in cosmids pV dSgr d4 and pV dSgr 4gB, the SgrA1 fragment spanning the internal nucleotides (from nucleotides 777 through 28743) was isolated by digestion of pV Fsp4 with SgrA1 and an agarose gel electrophoresis. This fragment was inserted into either SgrA1 digested pV dSgr d4 or SgrA1 digested pV dSgr 4gB. Following ligation, the cosmids were packaged using a lambda packaging extract (Gigapack, Stratagene) and used to infect E. coli. The resulting cosmids, pV Fspdelta 4 and pV Fsp4gB, were identified by restriction enzyme digestion. These two cosmids were then used to regenerate VZV that contains either a deletion of the C-terminal 60% of ORF S/L or a VZV that contains a gB epitope at the C-terminus of ORF S/L.

EXAMPLE 8

Transfection of MeWO Cells Using the Four Cosmids Made with Overlapping Wildtype VZV (Oka) DNA Fragments to Produce Reconstructed Wildtype VZV The four cosmids prepared with overlapping VZV DNA fragments (pV Fsp4, pV Spe 5, pV Pme 19, and pV Spe21), as described above, were used to transfect MeWO cells and produce reconstructed wildtype VZV. As an alternative to MeWO Cells, MRC-5, WI-38, human foreskin fibroblast cells could be used with cosmids pV Fsp4, pV Spe5, pV Pme19, and pV Spe21 or other cosmids described herein containing mutant ORFS/L genes.

Prior to transfection, cosmids pV Fsp4, pV Spe5, pV Pme19 and pV Spe21, were prepared from E. coli using techniques known in the art and digested with AscI to release the overlapping VZV AscI adapted fragments from each cosmid. AscI was chosen because there were no AscI sites found in the VZV Oka strain. Approximately 10 µg of pV Fsp 4, pV Spe 5, and pV Pme 19 and 5 µg of pV Spe21 cosmid DNA were separately digested with AscI. After digestion a small aliquot from each digest was removed to confirm on agarose gel electrophoresis that digestion was complete. The remainder of the digests, containing cosmid DNA and overlapping VZV AscI adapted fragments, were combined in a final solution of 10 mM EDTA to arrest AscI activity.

The combined cosmid DNA and overlapping VZV AscI adapted fragments ("combined DNA") were co-purified by 3 extractions with equal volumes of phenol and chloroform (chloroform is actually 24 parts chloroform and 1 part iso-amyl alcohol) followed by one extraction with chloroform. The combined DNA was precipitated by the addition of sodium acetate to 0.3 M and 3 volumes of ethanol. The combined DNA pellet was collected by centrifugation for 10 minutes and then washed with 70% ethanol. The ethanol was removed and the combined DNA was resuspended in water, generally at 350 ng/μl (total combined DNA content).

For transfection of MeWO cells, at least 3 μg of combined DNA (mixed as described above) and 0 to 500 ng of the plasmid pMS62 were diluted into 250 μl of a CaCl$_2$ solution with a fnal concentration of 0.252 M. (The plasmid pMS62 is a plasmid that contains VZV ORF62 under transcriptional control of the CMV major immediate early promoter. This plasmid increases the reliability of generating infectious VZV using this transfection system. See, Cohen, J. I. and Seidel, K. E., *Proc. Natl. Acad. Sci.* 90:7376–7380 (1993). The combined DNA/CaCl$_2$ solution was slowly added to an equal volume of Hepes buffered saline (280 mM NaCl; 10 mM KCl; 1.4 mM Na$_2$HPO$_4$,, 5.6 mM glucose; 20 mM HEPES, pH 7.05) to form a precipitate which was then incubated in the buffer for 30 minutes at room temperature. After aspiration to remove culture media, the combined DNA precipitates were added to cells plated on an approximately 25 cm$^2$ surface area for 500 μl of combined DNA solution. (The MeWO cells were trypsinized 24 hours prior to the transfection procedure and seeded with 2×10$^6$ MeWO cells per 25 cm$^2$.) Culture media was placed on the cells and they were returned to an incubator for 2 to 6 hours. At this time, the cells were subjected to a glycerol shock as known in the art. In brief, 3 mls of 15% glycerol in Hepes buffered saline was added for 3 min at 37° C. The glycerol solution was removed, the cells rinsed once with media and 5 ml of media was added. The cells were then assayed for plaque development after growth for 3–5 days. Optionally, no glycerol shock was performed and the cells were assayed for plaque development after growth for 3–5 days.

The MeWO cells were assayed for plaque formation as follows: Three to five days post-transfection, the cells are trypsinized to release the cells from the culture dish and reseeded in a vessel containing 3 times more surface area than the culture dish. Three to six days following the trypsinization, the larger vessels were monitored for plaque formation with a light microscope that allows visual scoring of plaques. Alternatively, the cells can be stained by rinsing twice with water and plaques can be visualized with a light microscope and counted more accurately compared to non stained cells.

Using this assay method, the disclosed method of reconstructing VZV produced 250 plaques of reconstructed VZV using 3.5 μg of total cosmid DNA with 50 ng of pMS62; 450 plaques of reconstructed VZV using 3.5 μg of total cosmid DNA with 500 ng of pMS62; greater than 1,000 plaques (nearly confluent) reconstructed VZV using 7.0 μg of DNA cosmid DNA with 50 ng of pMS62. The ratio of cosmids used with overlapping fragments (for total cosmid DNA) was 1:1:1:0.5 (pV Fsp4, pV Spe5, pV Pme 19 and pV Spe21, respectively).

In addition to making reconstructed wild type Oka VZV, this technique can be used with ORFS/L gene fragments produced from deletions, such as, but not limited to, the ApaL deletion described in Example 7, or ORFS/L gene mutations as discussed herein, to make reconstructed mutant VZV.

EXAMPLE 9

Northern Analysis of RNA from VZV (Oka) Infected Cells Demonstrates the Presence of a ORFS/L Gene Transcript Human foreskin fibroblast (HF) cells infected with wild-type VZV (Oka) were tested for the presence of an ORFS/L gene transcript follows. PCR was used with the primer pair "ORFS/LPr2" and ORFS/LPr1" on DNA isolated from the cytoplasm of VZV (Oka) infected HF cells to make a probe fragment.

Primer ORFS/LP 1 had the following sequence:

5'-GCCGCCATGGGATGAAAAAAGTGTCT-GTCTGTCTGTGCG-3'    SEQ ID NO: 7

Primer ORFS/LP 2 had the following sequence:

5'-GCCGCC ATGGTCATGTAGTTGAGTTGGGAG SEQ ID NO: 8

PCR was performed using these two primers in accordance with the manufacturer's instructions (Gene Amp, Perkin-Elmer).

A DNA fragment ("PCR DNA") of the appropriate size was generated from the PCR. The PCR DNA was digested with NcoI (the site had been incorporated into the 5' region of both ORFS/LPr1 and ORFS/LPr2) and inserted into NcoI digested plasmid pGEM5zf+. The resulting plasmid was designated pORFS/L C7. The vector pGEM5zf+ contains the phage Sp6 and T7 RNA promoters on either side of the NcoI site.

Two different synthetic runoff $^{32}$P-labeled RNA transcripts were made from pORFS/L C7 to use as probes of HF cell RNA.

The first probe was designated Sp6/EcoRI. pORFS/L C7 was digested with EcoRI and transcribed using Sp6 RNA polymerase and |$^{32}$P| CTP according to the manufacturer's instructions (Promega, Madison, Wis.). The $^{32}$P labeled RNA that was generated was the appropriate size (approximately 650 nucleotides) and predicted to be the same sense as an ORFS/L transcript.

The second probe was designated T7/Xho. pORFS/L C7 was digested with XhoI and transcribed using T7 RNA polymerase and |$^{32}$P| CTP according to the manufacturer's instructions (Promega, Madison, Wis.). The $^{32}$P labeled RNA that was generated was the appropriate size (approximately 580 nucleotides) and predicted to be complementary to an ORFS/L transcript.

The RNA used in these experiments was from HF cells. Six 850 cm$^2$ roller bottles of confluent HF cells were infected with VZV (Oka). 3 days post infection the total RNA was harvested from the cells following the method of Chomczymunski and Sacchi, *Anal. Biochem.* 162:156 (1987). 3 roller bottles of uninfected HF were processed in parallel as control RNA.

Polyadenylated RNA was also made from total HF RNA. Approximately 1 mg of the harvested RNA was enriched for polyadenylated RNA by affinity chromatography on oligo dT cellulose (Boehringer Mannheim). Nonspecific species were washed from the column with a 20 mM Tris (pH7.5); solution containing 1 M LiCl, 0.2% SDS, and 2 mM EDTA. Specifically bound polyA RNA was eluted with 10 mM Tris (pH 7.5), 1 mM EDTA, 0.0–5% SDS.

Total and polyadenylated RNA from infected and uninfected cells was separated by size on a 1% agarose/6.6% formaldehyde gel using electrophoresis. The following samples were loaded onto the gel.

1. 20 μg VZV infected HF whole cell RNA.
2. 20 μg VZV uninfected HF whole cell RNA.
3. 1 μg of VZV infected HF poly A enriched RNA.
4. 1 μg of VZV infected HF poly A depleted RNA.
5. 1 μg of uninfected HF poly A enriched RNA.
6. 1 μg of uninfected HF poly A depleted RNA.

Following electrophoresis, these samples were transferred from the gel to Hybond N+ paper by capillary action, as a blot. The nucleic acids were then fixed to the Hybond by UV irradiation.

Duplicate samples of the RNA samples of the above gels and blots were made. One blot was incubated with the Sp6/EcoRI (same sense) probe as a control and its duplicate incubated with the T7/XhoI (complementary) probe. The hybridization conditions were: 6×SSC; 1/×Denhardts; 30% foramide; 0.1 mg/ml single stranded sheared salmon sperm DNA at 58° C. for 17 hours. Unhybridized probe was washed off with 1.0×SSC; 0.1% SDS at 58° C. for 15 min followed by 0.1×SSC; 0.1% SDS at 58° C. for 15 min. In order to increase the specificity of the probe that remained bound, the filters were then washed 3 times in 2×SSC, incubated in 1 µg/ml RNAse A in 2×SSC for 15 min at room temperature, followed by a fmal wash in 0.1×SSC; 0.1% SDS at 50° C. for 45 minutes. The washed, hybridized blots were exposed to X-ray film and developed at various intervals.

The washed, hybridized blots yielded the following results:

| HF RNA Sample | Sp6/EcoRI Probe | T7/XhoI Probe |
|---|---|---|
| VZV Whole Cell | – | + |
| Uninfected Whole Cell | – | – |
| VZV Poly A enriched | – | + |
| VZV Poly A depleted | – | – |
| Uninfected Poly A enrich | – | – |
| Uninfected poly A depleted | – | – |

An "–" indicates no band was observed and a "+" indicates a band was observed. The analysis indicated that a polyadenylated RNA of approximate 780 nucleotides was present in VZV (Oka) infected HF. Because the T7/XhoI probe is antisense to the predicted ORFS/L mRNA, the RNA that is being detected in these cells is the same sense as the predicted ORFS/L mRNA. A shorter probe that was derived entirely from the C-terminal region of ORFS/L and used to determine the size of ORFS/L gene transcripts in Northern blots also produced results consistent with this result (data not shown). Because of the location of the open reading frames in VZV, ORFS/L is the only good candidate to be encoded by this transcript. The transcript size of the ORFS/L gene was 800–900 bases in length.

EXAMPLE 10

Expression of ORFS/L (Oka) Proteins

To express different ORFS/L proteins from the ORFS/L gene of Oka the following plasmids, described herein, were used:

pV4L (genomic clone encoding a 157 amino acid ORFS/L protein), pG S/L C3 (PCR clone encoding a 223 amino acid ORFS/L protein), and pG ORFS/L-CgB7 (PCR clone mutant encoding a 205 amino acid ORFS/L protein with 37 C-terminal amino acids replaced with 20 amino acids from the CMV gB epitope).

The plamids were used with a cell free transcription/translation system by Promega (TnT T7 Coupled Reticulocyte Lysate System). All reactions were carried out according to the manufacturers directions. Plasmid DNA, used for the these experiments, was prepared according to standard techniques known in the art. RNA was prepared in the complex transcription/translation reactions reaction using either T7 or SP6 RNA polymerase as indicated. The transcription/translation reactions included, in addition to the above test plasmids, a number of negative and positive controls to ensure that the expression system was working correctly. The controls used were the luciferase control plasmid (supplied by Promega), no DNA, antisense DNA for the entire ORFS/L gene from the PCR clone, and the $\gamma_1$ 34.5 gene from herpes simplex virus (pG ICP 34.5).

In addition, the translation products of the ORFS/L gene from plasmids pG S/L C3 and pG ORF S/LCgB-7 were subjected to immunoprecipitation using a mouse monoclonal antibody that reacts with the CMV gB epitope. Following in vitro transcription/translation of reactions containing the two plasmids pG S/L C3 and pG ORF S/LCgB-7, aliquots were separately removed and the extracts were separately incubated with a mouse monoclonal antibody that reacts with the CMV gB epitope. This antibody, #1201, was purchased from the Goodwin Institute for Cancer Research, Inc. (Other designation for this antibody found in the literature is CH28). 1 ul of the antibody was incubated with each extract from the two transcription/translation reactions for 30 minutes at room temperature. 10 ul of a 50% slurry of CL4B sepharose-crosslinked protein A was added to each antibody incubation and further incubated for 30 minutes at room temperature. Each sepharose sample was pelleted by a 10 second spin in a microfuge and washed after successive spins as follows: twice in 0.6M NaCl/50 mM Tris pH 7.5 (500 ul), once in 0.1% SDS/0.05% NP40/10 mM Tris pH 8.0/0.3M NaCl (500 ul), once in 0.6 M NaCl/50 mM Tris pH 7.5 (500 ul), once in 0.3M NaCl/50 mM Tris pH 7.5 (500 ul), and once in 20 mM Tris pH 8.3 (500 ul). Each pellet was then resuspended in 10 ul of $H_2O$.

Samples from each transcription/translation reaction and samples from each immunoprecipitation were then subjected to gel electrophoresis as follows. 10 ul of sample buffer was added to 10 ul of each sample (Sample buffer is 100 mM DTT, 125 mM Tris (pH 7.0) 15% sucrose 4% SDS, 1 mM EDTA and 0.01% bromophenol blue). The samples were heated at 90° C. for 5 minutes and loaded onto a discontinuous SDS-polyacrylamide gel (a 12.5% resolving gel) and electrophoresed at constant current. Following electrophoresis, the gel was fixed with 25% isopropanol and 10% acetic acid for 30 minutes, incubated with the fluor solution AMPLIFY (purchased from Amersham), and dried onto Whatmann paper. The gel was exposed to Hyperfilm MP (Amersham) and machine developed.

The results of the transcription/translation reactions and the immunoprecipitations are shown in FIG. 8. The lanes in FIG. 8 contain the following samples:

1. Luciferase positive control plasmid using T7 RNA polymerase,
2. No DNA using 17 RNA polymerase and Sp6 RNA polymerase,
3. pG S/L C3 (entire ORFS/L C3) using Sp6 RNA polymerase,
4. pG S/L C3 antisense control (entire ORFS/L C3) using T7 RNA polymerase,
5. pG ORFS/L-CgB-7 (ORFS/L protein with CMV epitope) using Sp6 RNA polymerase,
6. pV4L (first ORF) using 17 RNA polymerase,
7. pG ICP34.5 (herpes simplex viral protein) using Sp6 RNA polymerase,
8. pG S/L C3 (subjected to immunoprecipitation) using Sp6 RNA polymerase, and
9. pQ ORFS/L-CgB-7 (subjected to immunoprecipitation) using Sp6 RNA polymerase.

The Sp6 transcripts from pG S/L C3, pG ORF S/L-CgB7, and pG ICP34.5 generated proteins corresponding to ORF S/L (41 kd and 28 kd bands), ORF S/L-gB (32 kd band), and $\gamma_1$ 34.5 (42 kd band) proteins, respectively. The 17 transcripts of the Luciferase control plasmid and pV4L generated proteins correspond to firefly luciferase (62 kd) and ORFS/L protein initiated at the ATG (288 kd band), respectively. The 1 RNA generated from pG S/L C3 was an antisense orientation of the ORFS/L gene and old protein encode an ORFS/L .

EXAMPLE 11

Testing for VZV Growth in Cell of Non-Neuronal Tissue Origin and Attenuated Neurovirulence The reconstructed VZV and reconstructed mutant VZV of examples 7 and 8 can be tested for retention of VZV growth properties and efficient replication of the wild type VZV in cells from non-neuronal tissues and attenuated neurovirulence.

These properties can be assayed in cell culture. The $\gamma_1$34.5 deletion mutant of herpes simplex virus does not grow as well as the parental virus in the neuroblastoma cell line SK-N-SH as in J. Chou and B. Roizman, *Proc. Natl. Acad. of Sci.* (1992) 84:3266–3270, the methods of which are herein incorporated by reference. A modified version of this test is as follows.

The ability of a mutation to affect viral growth in neuronal tissue cells is determined using plague assays to measure VZV propagation. Growth curves of wild type VZV (Oka) and the modified VZV compositions of the present invention are generated and compared by measuring infective titers at various times post-infection using standard viral plaque forming assays known in the art. Mutant VZV is generated by cotransfecting MeWO cells with overlapping VZV fragments from cosmid clones as in examples 7 and 8. After cotransfection, infected cells develop plaques and a stock of the virus is made by treating the infected MeWO cells with trypsin to release the cells into the culture media. The cells are then used as an inoculum for human foreskin fibroblast (HF) cells. Separate HF cell cultures are infected with wild type VZV and modified VZV of the present invention. After incubation for 3 days at 34° C. trypsin is added to the HF cell cultures and viral stocks are prepared from each culture allocated and stored.

Aliquots of viral stock (wildtype or mutant VZV) are then used to infect cultures of "tester" cells. The tester cells include the human nueroblastoma cell line SK-N-SH, or other human or murine neuroblastoma cell lines. At designated points 1–5 days following infection, the neuroblastoma cells are subjected to treatment with trypsin and various concentrations of the trypsin treated cells are then added to a confluent monolayer of MeWO cells, which form plaques after infection. Three to five days after infection, the MeWO cell monolayers infected with wild type or modified VZV infection reaches a maximum, the plaques are counted and the virus titer is determined. The modified VZV titer will be compared to the wild type virus titer in permissive cells (MRC-5 or VERO cells) and "tester" cells. Thus, dual comparison provides an indication of the ability of the modified VZV to grow on the "tester" cells and permissive cells. Serum conditions can be adjusted to improve the titer yield, See PCT application WO 93/24616. An ORFS/L gene mutation decreases the plaque forming units (PFU) obtained from cells of neuronal tissue origin. A mutation of the ORFS/L gene preferably decreases the PFU at least 10 fold, more preferably at least 100 fold, and most preferably by at least 1,000 fold compared to the wild type VZV.

Comparison of the titers and recombinant and parental virus will reveal the presence or absence of a growth defect in this cells line.

It is anticipated that mutant VZV will grow more poorly in SK-N-SH cells than the parental virus (wild type), yet will grow comparable to the parental virus in cells not of neuronal origin (such as VERO cells). Mutations of the ORFS/L gene that result in 30% slower growth in SK-N-SH, compared to the parent virus are preferred.

Biological Deposits

DNA samples containing four plasmids pG S/L C3, pV4L, pV21S, and pV 21J were deposited with American Type Culture Collection, 12301 Parlawn Drive, Rockville, Md. 20852 (ATCC Accession Number 75758, 75757, 75755 and 75756, respectively).

I claim:

1. An isolated or recombinant protein comprising an amino acid sequence selected from the group consisting of the sequences enumerated in SEQ ID NO:12 and 14.

2. A mutant ORFS/L protein that confers attenuated neurovirulence on a VZV strain making said mutant ORFS/L protein, which mutant ORFS/L protein comprises a mutation that is not present in an ORFS/L protein of a naturally occurring VZV strain, wherein said mutation comprises a deletion of amino acids 99 through 223 of SEQ ID NO:12, and wherein neurovirulence is attenuated as compared to a naturally occurring VZV strain.

3. A mutant ORFS/L protein that confers attenuated neurovirulence on a VZV strain making said mutant ORFS/L protein, which mutant ORFS/L protein comprises a mutation that is not present in an ORFS/L protein of a naturally occurring VZV strain, wherein said mutation comprises a deletion of amino acids 121 through 157 of SEQ ID NO:14 and replacement of said amino acids with 20 amino acids from a heterologous viral protein not encoded by a genome of a naturally occurring VZV strain, and wherein neurovirulence is attenuated as compared to a naturally occurring VZV strain.

4. A mutant ORFS/L protein according to claim 3, wherein said heterologous viral protein is a CMV gB protein.

5. A mutant ORFS/L protein that confers attenuated neurovirulence on a VZV strain making said mutant ORFS/L protein, which mutant ORFS/L protein comprises a mutation that is not present in an ORFS/L protein of a naturally occurring VZV strain, wherein said mutation comprises a deletion of at least 10 amino acids,
    wherein neurovirulence is attenuated as compared to a naturally occurring VZV strain.

6. A mutant ORFS/L protein according to claim 5, the deletion comprising at least 10 contiguous amino acids.

7. A mutant ORFS/L protein according to claim 5, wherein the deleted amino acids include at least one functional site selected from the group consisting of: a cAMP phosphorylation site, a myristylization site, a PKC phosphorylation site and a N-linked glycosylation site.

8. A mutant ORFS/L protein according to claim 5, wherein at least one deleted amino acid is substituted by a heterologous amino acid not encoded by a genome of a naturally occurring VZV strain.

* * * * *

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: Oligomer DNA (xi) SEQUENCE DESCRIPTION: SEQ ID NO: 1:

GCCGCCATGG AGGGGAGCGA CGGAACACG    29

(2) INFORMATION FOR SEQ ID NO: 2:

(i) SEQUENCE CHARACTERISTICS:

(A) LENGTH: 29 base pairs
            (B) TYPE: nucleic acid
            (C) STRANDEDNESS: single
            (D) TOPOLOGY: linear (ii) MOLECULE TYPE: Oligomer DNA (xi) SEQUENCE DESCRIPTION: SEQ ID NO: 2:

GCCGCCATGG CTGTCGGCGG ACTATGAAC                                              29

(2) INFORMATION FOR SEQ ID NO: 3:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: Oligomer DNA (xi) SEQUENCE DESCRIPTION: SEQ ID NO: 3:

GATCCGGCGC GCCA                                                              14

(2) INFORMATION FOR SEQ ID NO: 4:

(i) SEQUENCE CHARACTERISTICS:
            (A) LENGTH: 10 base pairs
            (B) TYPE: nucleic acid
            (C) STRANDEDNESS: single
            (D) TOPOLOGY: unknown (ii) MOLECULE TYPE: Oligomer DNA (xi) SEQUENCE DESCRIPTION: SEQ ID NO: 4:

TGGCGCGCCG                                                                   10

(2) INFORMATION FOR SEQ ID NO: 5:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (ii) MOLECULE TYPE: Oligomer DNA (xi) SEQUENCE DESCRIPTION: SEQ ID NO: 5:

CTAGGGTACC TTAGTGGCGA TATCCGTTCT TGCGGTGGCG GAGGCGGTCG                       50

AGGAGGTTGG GCTTCTGCCC CTT                                                    73

(2) INFORMATION FOR SEQ ID NO: 6:

(i) SEQUENCE CHARACTERISTICS:
            (A) LENGTH: 73 base pairs
            (B) TYPE: nucleic acid
            (C) STRANDEDNESS: single
            (D) TOPOLOGY: linear (ii) MOLECULE TYPE: Oligomer DNA (xi) SEQUENCE DESCRIPTION: SEQ ID NO: 6:

AATTAAGGGG CAGAAGCCCA ACCTCCTCGA CCGCCTCCGC CACCGCAAGA                       50

ACCGATATCG CCACTAAGGT ACC                                                    73

(2) INFORMATION FOR SEQ ID NO: 7:

(i) SEQUENCE CHARACTERISTICS:

(A) LENGTH: 39 base pairs
        (B) TYPE: nucleic acid
        (C) STRANDEDNESS: single
        (D) TOPOLOGY: linear (ii) MOLECULE TYPE: Oligomer DNA (xi) SEQUENCE DESCRIPTION: SEQ ID NO: 7:

GCCGCCATGG GATGAAAAAA GTGTCTGTCT GTCTGTGCG            39

(2) INFORMATION FOR SEQ ID NO: 8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Oligomer DNA (xi) SEQUENCE DESCRIPTION: SEQ ID NO: 8:

GCCGCCATGG TCATGTAGTT GAGTTGGGAG GTTCC                35

(2) INFORMATION FOR SEQ ID NO: 9:

(i) SEQUENCE CHARACTERISTICS:
        (A) LENGTH: 1126 base pairs
        (B) TYPE: nucleic acid
        (C) STRANDEDNESS: double
        (D) TOPOLOGY: unknown (ii) MOLECULE TYPE: DNA (Genomic)

(ix) FEATURE:
        (A) NAME/KEY: CDS
        (B) LOCATION: 90...761

(xi) SEQUENCE DESCRIPTION: SEQ ID NO: 9:

AGAGTCGGGG GTGACGGAGT CCCCTCCTTT TCTCGTGAGC GCCACTGGCG CGCGGACTGT            60

TTGTTGTTAA TAAAAGCGGA ACGGTTTTT ATG AAA AAA GTG TCT GTC TGT CTG            113
                                Met Lys Lys Val Ser Val Cys Leu
                                  1               5

TGC GGG CGG GCG ACG GGC GGG CTG GTC GGA CCC CCC CCC GAA AAT AAC            161
Cys Gly Arg Ala Thr Gly Gly Leu Val Gly Pro Pro Pro Glu Asn Asn
 10              15                  20

CCC CCC CCG GTT TCT GGG CGC CCG GCG GAC CCC GGG AGA GGA GGC CAG            209
Pro Pro Pro Val Ser Gly Arg Pro Ala Asp Pro Gly Arg Gly Gly Gln
25              30                  35                  40

CCC TCT CGC GGC CCC CTC GAG AGA GAA AAA AAA AAG CGA CCC CAC CTC            257
Pro Ser Arg Gly Pro Leu Glu Arg Glu Lys Lys Lys Arg Pro His Leu
            45                  50                  55

CCC GCG CGT TTG CGG GGC GAC CAT CGG GGG GGA TGG GAT TTT TTG CCG            305
Pro Ala Arg Leu Arg Gly Asp His Arg Gly Gly Trp Asp Phe Leu Pro
        60                  65                  70

GGA AAC CCC CCC CCG CCA GCC TTT AAC AAA ACC CGC GCC TTT TGC GTC            353
Gly Asn Pro Pro Pro Pro Ala Phe Asn Lys Thr Arg Ala Phe Cys Val
    75                  80                  85

CAC CCC TCG TTT ACT GCT CGG ATG GCG ACC GTG CAC TAC TCC CGC CGA            401
His Pro Ser Phe Thr Ala Arg Met Ala Thr Val His Tyr Ser Arg Arg
90                  95                  100

CCT GGG ACC CCG CCG GTC ACC CTC ACG TCG TCC CCC AGC ATG GAT GAC            449
Pro Gly Thr Pro Pro Val Thr Leu Thr Ser Ser Pro Ser Met Asp Asp
105                 110                 115                 120

GTT GCG ACC CCC ATC CCC TAC CTA CCC ACA TAC GCC GAG GCC GTG GCA            497
Val Ala Thr Pro Ile Pro Tyr Leu Pro Thr Tyr Ala Glu Ala Val Ala

-continued

```
                    125                  130                     135
GAC GCG CCC CCC CCT TAC AGA AGC CGC GAG AGT CTG GTG TTC TCC CCG    545
Asp Ala Pro Pro Pro Tyr Arg Ser Arg Glu Ser Leu Val Phe Ser Pro
            140                 145                 150

CCT CTT TTT CCT CAC GTG GAG AAT GGC ACC ACC CAA CAG TCT TAC GAT    593
Pro Leu Phe Pro His Val Glu Asn Gly Thr Thr Gln Gln Ser Tyr Asp
            155                 160                 165

TGC CTA GAC TGC GCT TAT GAT GGA ATC CAC AGA CTT CAG CTG GCT TTT    641
Cys Leu Asp Cys Ala Tyr Asp Gly Ile His Arg Leu Gln Leu Ala Phe
            170                 175                 180

CTA AGA ATT CGC AAA TGC TGT GTA CCG GCT TTT TTA ATT CTT TTT GGT    689
Leu Arg Ile Arg Lys Cys Cys Val Pro Ala Phe Leu Ile Leu Phe Gly
185                 190                 195                 200

ATT CTC ACC CTT ACT GCT GTC GTG GTC GCC ATT GTT GCC GTT TTT CCC    737
Ile Leu Thr Leu Thr Ala Val Val Val Ala Ile Val Ala Val Phe Pro
                205                 210                 215

GAG GAA CCT CCC AAC TCA ACT ACA TGAAACTACT GTCCGGAAGG GGAAGGTATT    791
Glu Glu Pro Pro Asn Ser Thr Thr
                220

TATTCTCGCT TGCAGCTTGT CGCGCGTGTA TGCACAACAA AAGCTATAAT ATGTCACCAA    851

AGCCAACGTC GCCATCTGGA GTACTACACC CAGTACGTTG CATAACCTGT CCATTTGCAT    911

TTTCAGTTGC GCGGACGCCT TTCTCCGGGA TCGTGGCCTT GGGACATCAA CCAGTGGAAT    971

AAGAACCGCC GGTGGTCTTG TTTGAACGAC GAGTGGCGAC GCGTTGTTCT GCATAAGCTC   1031

TGTATGCTGA TACATAAACA CAGAGTCTGT ATCGCTATCA GATTCCCGAA CACCTTCCGG   1091

TACCCCATAC TCCGATACCC TGGACATTGC GGATC                              1126
```

(2) INFORMATION FOR SEQ ID NO: 10:

(i) SEQUENCE CHARACTERISTICS:
        (A) LENGTH: 224 amino acids
        (B) TYPE: amino acid
        (D) TOPOLOGY: unknown (ii) MOLECULE TYPE: Protein (xi) SEQUENCE DESCRIPTION: SEQ ID NO: 10:

```
Met Lys Lys Val Ser Val Cys Leu Cys Gly Arg Ala Thr Gly Gly Leu
 1               5                  10                  15

Val Gly Pro Pro Glu Asn Asn Pro Pro Val Ser Gly Arg Pro
                20                  25                  30

Ala Asp Pro Gly Arg Gly Gly Gln Pro Ser Arg Gly Pro Leu Glu Arg
                35                  40                  45

Glu Lys Lys Arg Pro His Leu Pro Ala Arg Leu Arg Gly Asp His
    50                  55                  60

Arg Gly Gly Trp Asp Phe Leu Pro Gly Asn Pro Pro Pro Ala Phe
65                  70                  75                  80

Asn Lys Thr Arg Ala Phe Cys Val His Pro Ser Phe Thr Ala Arg Met
                85                  90                  95

Ala Thr Val His Tyr Ser Arg Arg Pro Gly Thr Pro Val Thr Leu
                100                 105                 110

Thr Ser Ser Pro Ser Met Asp Asp Val Ala Thr Pro Ile Pro Tyr Leu
                115                 120                 125

Pro Thr Tyr Ala Glu Ala Val Ala Asp Ala Pro Pro Tyr Arg Ser
    130                 135                 140

Arg Glu Ser Leu Val Phe Ser Pro Pro Leu Phe Pro His Val Glu Asn
145                 150                 155                 160
```

Gly Thr Thr Gln Gln Ser Tyr Asp Cys Leu Asp Cys Ala Tyr Asp Gly
                165                 170                 175

Ile His Arg Leu Gln Leu Ala Phe Leu Arg Ile Arg Lys Cys Cys Val
            180                 185                 190

Pro Ala Phe Leu Ile Leu Phe Gly Ile Leu Thr Leu Thr Ala Val Val
        195                 200                 205

Val Ala Ile Val Ala Val Phe Pro Glu Glu Pro Asn Ser Thr Thr
    210                 215                 220

(2) INFORMATION FOR SEQ ID NO: 11:

(i) SEQUENCE CHARACTERISTICS:
        (A) LENGTH: 1121 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO: 11:

```
AGTCGGGGGT GACGGAGTCC CCTCCTTTTC TCGTGASCCA CTGGCGCGCG GACTGTTTGT      60

TGTTTGTTAA TAAAAGCGGA ACGGTTTTTA TGAAAAAAGT GTCTGTCTGT CTGTGCGGGC     120

GGGCGACGGG CGGGCTGGTC GGACCCCCCC CGAAAATAAC CCCCCCCGGT TTCTGGGCGC     180

CCGGCGGACC CCGGGGGGGG GGCCCAGCCC TCTCGCGGCC CCCTCGAGAG AGAAAAAAAA     240

AAGCGACCCC ACCTCCCCGC GCGTTTGCGG GGCGACCATC GGGGGGGATG GGATTTTTTG     300

CCGGGAAACC CCCCCCGCCA GCCTTTAACA AAACCCGCGC CTTTTGCGTC CACCCCTCGT     360

TTACTGCTCG GATGGCCACC GTGCACTACT CCCGCCGACC TGGGACCCCG CCGGTCACCC     420

TCACGTCGTC CCCCGGCATG GATGACGTTG CGACCCCCAT TCCCTACCTA CCCACATACG     480

CCGAGGCCGT GGCAGACGCG CCCCCCCCTT ACAGAAGCCG CGAGAGTCTG GTGTTCTCCC     540

CGCCTCTTTT TCCTCACGTG GAGAATGGCA CCACCCAACA GTCTTACGAT TGCCTAGACT     600

GCGCTTATGA TGGAATCCAC AGACTTCAGC TGGCTTTTCT AAGAATTCGC AAATGCTGTG     660

TACCGGCTTT TTTAATTCTT TTTGGTATTC TCACCCTTAC TGCTGTCGTG GTCGCCATTG     720

TTGCCGTTTT TCCCGAGGAA CCTCCCAACT CAACTACATG AAACTACTGT CCGGAAGGGA     780

AGGTATTTAT TCTGCTTGCA GCTTGTCGCG CGTGTATGCA CAACAAAGC  TATATATGTC     840

ACCAAAGCCA ACGTCGCCAT CTGGAGTACT ACACCCAGTA CATTGCATAA CCTGTCCATT     900

TGCATTTTCA GTTGCGCGGA CGCCTTTCTC CGGGATCGTG GCCTTGGGAC ATCAACCAGT     960

GGAATAAGAA CCGCCGGTGG TCTTGCCCGA ACGACGAGTG GCGACGCGTT GTTCTGCATA    1020

AGCTCTGTAT GCTGATACAT AAACACAGAG TCTGTATCGC TATCAGATTC CCGAACACCT    1080

TCCGGTACCC CATACTCCGA TACCCTGGAC ATTGCGGATC C                       1121
```

(2) INFORMATION FOR SEQ ID NO: 12:

(i) SEQUENCE CHARACTERISTICS:
        (A) LENGTH: 223 amino acids
        (B) TYPE: amino acid
        (D) TOPOLOGY: unknown (ii) MOLECULE TYPE: Protein (xi) SEQUENCE DESCRIPTION: SEQ ID NO: 12:

Met Lys Lys Val Ser Val Cys Leu Cys Gly Arg Ala Thr Gly Gly Leu
1               5                   10                  15

```
Val Gly Pro Pro Pro Lys Ile Thr Pro Pro Gly Phe Trp Ala Pro Gly
            20                  25                  30

Gly Pro Arg Gly Gly Gly Pro Ala Leu Ser Arg Pro Pro Arg Glu Arg
        35                  40                  45

Lys Lys Lys Ala Thr Pro Pro Pro Arg Ala Phe Ala Gly Arg Pro Ser
    50                  55                  60

Gly Gly Met Gly Phe Phe Ala Gly Lys Pro Pro Pro Ala Phe Asn
65                  70                  75                  80

Lys Thr Arg Ala Phe Cys Val His Pro Ser Phe Thr Ala Arg Met Ala
                85                  90                  95

Thr Val His Tyr Ser Arg Arg Pro Gly Thr Pro Pro Val Thr Leu Thr
            100                 105                 110

Ser Ser Pro Gly Met Asp Asp Val Ala Thr Pro Ile Pro Tyr Leu Pro
        115                 120                 125

Thr Tyr Ala Glu Ala Val Ala Asp Ala Pro Pro Tyr Arg Ser Agr
    130                 135                 140

Glu Ser Leu Val Phe Ser Pro Pro Leu Phe Pro His Val Glu Asn Gly
145                 150                 155                 160

Thr Thr Gln Gln Ser Tyr Asp Cys Leu Asp Cys Ala Tyr Asp Gly Ile
                165                 170                 175

His Arg Leu Gln Leu Ala Phe Leu Arg Ile Arg Lys Cys Cys Val Pro
            180                 185                 190

Ala Phe Leu Ile Leu Phe Gly Ile Leu Thr Leu Thr Ala Val Val Val
        195                 200                 205

Ala Ile Val Ala Val Phe Pro Glu Glu Pro Pro Asn Ser Thr Thr
    210                 215                 220

(2) INFORMATION FOR SEQ ID NO: 13:

(i) SEQUENCE CHARACTERISTICS:
        (A) LENGTH: 561 base pairs
        (B) TYPE: nucleic acid
        (C) STRANDEDNESS: double
        (D) TOPOLOGY: unknown (ii) MOLECULE TYPE: DNA (Genomic)

(xi) SEQUENCE DESCRIPTION: SEQ ID NO: 13:

GGCCCAGCCC TCTCGCGGCC CCCTCGAGAG AGAAAAAAAA AAGCGACCCC ACCTCCCCGC    60

GCGTTTGCGG GGCGACCATC GGGGGGGATG GGATTTTTTG CCGGGAAACC CCCCCCGCCA   120

GCCTTTAACA AAACCCGCGC CTTTTGCGTC CACCCCTCGT TTACTGCTCG GATGGCCACC   180

GTGCACTACT CCCGCCGACC TGGGACCCCG CCGGTCACCC TCACGTCGTC CCCCGGCATG   240

GATGACGTTG CGACCCCCAT TCCCTACCTA CCCACATACG CCGAGGCCGT GGCAGACGCG   300

CCCCCCCCTT ACAGAAGCCG CGAGAGTCTG GTGTTCTCCC CGCCTCTTTT TNCTCACGTG   360

GAGAATGGCA CCACCCAACA GTCTTACGAT TGCCTAGACT GCGCTTATGA TGGAATCCAC   420

AGACTTCAGC TGGCTTTTCT AAGAATTCGC AAATGCTGTG TACCGGCTTT TTTAATTCTT   480

TTTGGTATTC TCACCCTTAC TGCTGTCGTG GTCGCCATTG TTGCCGTTTT TCCCGAGGAA   540

CCTCCCAACT CAACTACATG A                                            561

(2) INFORMATION FOR SEQ ID NO: 14:

(i) SEQUENCE CHARACTERISTICS:
        (A) LENGTH: 157 amino acids
        (B) TYPE: amino acid
        (D) TOPOLOGY: unknown
```

(ii) MOLECULE TYPE: Protein (xi) SEQUENCE DESCRIPTION: SEQ ID NO: 14:

Met Gly Phe Phe Ala Gly Lys Pro Pro Pro Ala Phe Asn Lys Thr
1               5                   10                  15

Arg Ala Phe Cys Val His Pro Ser Phe Thr Ala Arg Met Ala Thr Val
                20                  25                  30

His Tyr Ser Arg Arg Pro Gly Thr Pro Pro Val Thr Leu Thr Ser Ser
            35                  40                  45

Pro Gly Met Asp Asp Val Ala Thr Pro Ile Pro Tyr Leu Pro Thr Tyr
        50                  55                  60

Ala Glu Ala Val Ala Asp Ala Pro Pro Tyr Arg Ser Arg Glu Ser
65                  70                  75                  80

Leu Val Phe Ser Pro Pro Leu Phe Pro His Val Glu Asn Gly Thr Thr
                85                  90                  95

Gln Gln Ser Tyr Asp Cys Leu Asp Cys Ala Tyr Asp Gly Ile His Arg
            100                 105                 110

Leu Gln Leu Ala Phe Leu Arg Ile Arg Lys Cys Cys Val Pro Ala Phe
            115                 120                 125

Leu Ile Leu Phe Gly Ile Leu Thr Leu Thr Ala Val Val Val Ala Ile
130                 135                 140

Val Ala Val Phe Pro Glu Glu Pro Pro Asn Ser Thr Thr
145                 150                 155

(2) INFORMATION FOR SEQ ID NO: 15:

(i) SEQUENCE CHARACTERISTICS:
        (A) LENGTH: 222 base pairs
        (B) TYPE: nucleic acid
        (C) STRANDEDNESS: double
        (D) TOPOLOGY: unknown (ii) MOLECULE TYPE: DNA (Genomic)

(xi) SEQUENCE DESCRIPTION: SEQ ID NO: 15:

GGCGGACTGT TGTTGTTTG TTAATAAAAG CGGAACGGTT TTTATGAAAA AAGTGTCTGT      60

CTGTCTGTGC GGGCGGGCGA CGGVCGGGCT GGTCGGACCC CCCCCGAAAA TAACCCCCCC    120

CGGTTTCTGG GCGCCCGGCG ACCCCGGGG GGGGGGGCCC AGCCCTCTCG CGGCCCCCTC    180

GAGAGAGAAA AAAAAAAGCG ACCCCACCTC HYCGCGCGTT TG                       222

(2) INFORMATION FOR SEQ ID NO: 16:

(i) SEQUENCE CHARACTERISTICS:
        (A) LENGTH: 207 base pairs
        (B) TYPE: nucleic acid
        (C) STRANDEDNESS: double
        (D) TOPOLOGY: unknown (ii) MOLECULE TYPE: DNA (Genomic)

(xi) SEQUENCE DESCRIPTION: SEQ ID NO: 16:

GTCAGAGTCG GGGGTGACGG AGTCCCCTCC TTTTCTCGTG AGCGCCACTG GCGCGCGGAC     60

TGTTTGTTGT TTGTTAATAA AGCGGAACG GTTTTTATGA AAAAGTGTC TGTCTGTCTG     120

TGCGNGCGGG CGACGGGCGG GCTGGTCGGA CCCCCCCCGA AAATAACCCC CCCCGGTTTC   180

TGGGCGCCCG GCGGACCCCG GGGGGGG                                        207

(2) INFORMATION FOR SEQ ID NO: 17:

(i) SEQUENCE CHARACTERISTICS:
    (A) LENGTH: 716 base pairs
    (B) TYPE: nucleic acid
    (C) STRANDEDNESS: double
    (D) TOPOLOGY: unknown (ii) MOLECULE TYPE: DNA (Genomic)

(xi) SEQUENCE DESCRIPTION: SEQ ID NO: 17:

```
GGCGGACTGT TTGTTGTTTG TTAATAAAAG CGGAACGGTT TTTATGAAAA AAGTGTCTGT      60
CTGTCTGTGC GGGCGGGCGA CGGVCGGGCT GGTCGGACCC CCCCCGAAAA TAACCCCCCC     120
CGGTTTCTGG GCGCCCGGCG GACCCCGGGG GGGGGGGCCC AGCCCTCTCG CGGCCCCCTC     180
GAGAGAGAAA AAAAAAAGCG ACCCCACCTC CCCGCGCGTT TGCGGGGCGA CCATCGGGGG     240
GGATGGGATT TTTTGCCGGG AAACCCCCCC CGCCAGCCTT TAACAAAACC CGCGCCTTTT     300
GCGTCCACCC CTCGTTTACT GCTCGGATGG CCACCGTGCA CTACTCCCGC CGACCTGGGA     360
CCCCGCCGGT CACCCTCACG TCGTCCCCCG GCATGGATGA CGTTGCGACC CCCATTCCCT     420
ACCTACCCAC ATACGCCGAG GCCGTGGCAG ACGCGCCCCC CCCTTACAGA AGCCGCGAGA     480
GTCTGGTGTT CTCCCCGCCT CTTTTTNCTC ACGTGGAGAA TGGCACCACC CAACAGTCTT     540
ACGATTGCCT AGACTGCGCT TATGATGGAA TCCACAGACT TCAGCTGGCT TTTCTAAGAA     600
TTCGCAAATG CTGTGTACCG GCTTTTTTAA TTCTTTTTGG TATTCTCACC CTTACTGCTG     660
TCGTGGTCGC CATTGTTGCC GTTTTTCCCG AGGAACCTCC CAACTCAACT ACATGA        716
```